United States Patent
Deane et al.

(10) Patent No.: US 10,786,593 B2
(45) Date of Patent: Sep. 29, 2020

(54) FLEXIBLE ELECTRODE ASSEMBLY FOR PLASMA GENERATION AND AIR TREATMENT SYSTEM INCLUDING THE FLEXIBLE ELECTRODE ASSEMBLY

(71) Applicant: Novaerus Patents Limited, Blackrock, Co. Dublin (IE)

(72) Inventors: Graham Deane, Blackrock (IE); Kevin Maughan, Blackrock (IE); Felipe Soberon, Blackrock (IE); Niall O'Connor, Blackrock (IE)

(73) Assignee: Novaerus Patents Limited, Dublin (IE)

( * ) Notice: Subject to any disclaimer, the term of this patent is extended or adjusted under 35 U.S.C. 154(b) by 0 days.

(21) Appl. No.: 15/503,211

(22) PCT Filed: Aug. 12, 2015

(86) PCT No.: PCT/EP2015/068605
§ 371 (c)(1),
(2) Date: Feb. 10, 2017

(87) PCT Pub. No.: WO2016/023964
PCT Pub. Date: Feb. 18, 2016

(65) Prior Publication Data
US 2017/0232132 A1 Aug. 17, 2017

(30) Foreign Application Priority Data
Aug. 12, 2014 (GB) .................................. 1414244.2

(51) Int. Cl.
*A61L 9/22* (2006.01)
*F24F 3/16* (2006.01)
(Continued)

(52) U.S. Cl.
CPC ..................................... *A61L 9/22* (2013.01);
*B03C 3/04* (2013.01); *B04C 9/00* (2013.01);
*F24F 3/166* (2013.01);
(Continued)

(58) Field of Classification Search
CPC .... A61L 9/22; B03C 3/04; B04C 9/00; B04C 2009/001; B04C 2009/005; F24F 3/166; F24F 2003/1682
See application file for complete search history.

(56) References Cited

U.S. PATENT DOCUMENTS

| 9,076,997 B2* | 7/2015 | Hirata ................ H01M 8/0206 |
| 2003/0108460 A1 | 6/2003 | Andreev |
| 2007/0144117 A1* | 6/2007 | Park ...................... B01D 45/12 |
| | | 55/345 |

FOREIGN PATENT DOCUMENTS

| EP | 1649923 | 4/2006 |
| WO | 9635521 | 11/1996 |

(Continued)

OTHER PUBLICATIONS

ISR from corresponding PCT/EP2015/068605.

*Primary Examiner* — Timothy C Cleveland
(74) *Attorney, Agent, or Firm* — Stephen T. Scherrer; Monique A. Morneault; Scherrer Patent & Trademark Law. P.C.

(57) ABSTRACT

A flexible electrode assembly for an air treatment device comprising: a flexible dielectric layer forming an insulating sheet; a plurality of conductive tracks on a first side of the insulating sheet; a conductive layer on a second side of the insulating sheet; wherein supply of voltage to the conducting tracks and the conductive layer generates plasma which is discharged from the conducting tracks. In a further aspect, the present invention also provides an air treatment apparatus for removal of health threatening airborne pollutants, which may include pathogens, from an air flow, the air treatment apparatus comprising an apparatus having a generally cyclonic-shaped geometry comprising a cylindrical (Continued)

section and a conical section. The present invention also relates to an air treatment device comprising the flexible electrode assembly.

6 Claims, 22 Drawing Sheets

(51) Int. Cl.
    *B04C 9/00*         (2006.01)
    *B03C 3/04*         (2006.01)

(52) U.S. Cl.
    CPC .. *B04C 2009/001* (2013.01); *B04C 2009/005* (2013.01); *F24F 2003/1682* (2013.01)

(56) References Cited

FOREIGN PATENT DOCUMENTS

| WO | 2004105820 | 12/2004 |
| WO | 2005037420 | 4/2005 |
| WO | 2008034605 | 3/2008 |

* cited by examiner

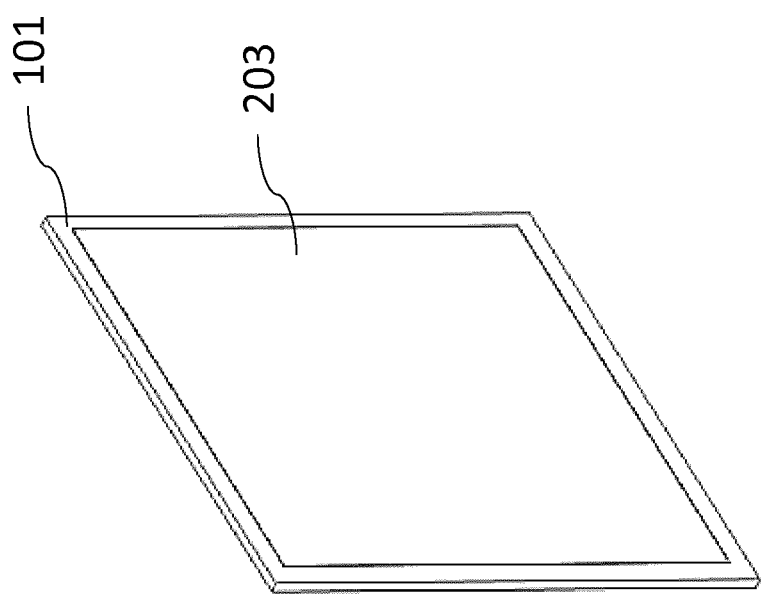
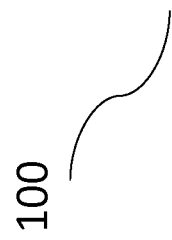
Figure 2

FLEXIBLE ELECTRODE ASSEMBLY FOR PLASMA GENERATION AND AIR TREATMENT SYSTEM INCLUDING THE FLEXIBLE ELECTRODE ASSEMBLY

FIELD

The present invention relates to an air treatment method and apparatus. More specifically, the invention relates to an air treatment apparatus comprising a flexible electrode assembly and an air ducting system. The apparatus may further comprise a power source. The electrode assembly is made of flexible materials and used to generate low power electrical discharge plasma for inactivating health threatening airborne pollutants present in indoor air and removing pollutants from the same. The present invention also provides a method of using such an apparatus in air treatment applications for removal of health threatening airborne pollutants.

In a further aspect, the present invention also provides an air treatment apparatus for removal of health threatening airborne pollutants, which may include pathogens, from an air flow, the air treatment apparatus comprising an apparatus having a generally cyclonic-shaped geometry comprising a cylindrical section and a conical section; the apparatus defining an area of generally circular fluid motion, rotating in the same direction, the apparatus having an air inlet for entry of air flow into the apparatus, and the air inlet being configured to facilitate establishing the generally circular fluid motion, and means being provided within the apparatus to inactivate the health threatening airborne pollutants and an exit from the apparatus from which purified outward air will exit. Ideally, in a preferred embodiment, the apparatus having a generally cyclonic-shaped geometry comprises the above defined flexible electrode assembly, with the flexible electrode assembly provided about the walls of the cyclonic-shaped geometry such that the air flow is directed towards the walls of the cyclonic-shaped apparatus such that the health threatening airborne pollutants are urged towards and into the inactivation zone created by the plasma discharged from the outward facing conductive layer of the flexible electrode assembly.

In another aspect, the present invention relates to an air treatment device comprising a plasma generating flexible electrode electrostatic precipitator assembly for air disinfection and pollution control wherein the plasma generating flexible electrode electrostatic precipitator assembly comprises the flexible electrode assembly configured for generating low power electrical discharge plasma and for inactivating pathogens in the air flow.

BACKGROUND

Health threatening airborne pollutants may be subdivided into three groups; (a) airborne pathogens comprising any organism that causes disease that spreads throughout the environment via the air; (b) airborne allergens comprising any substance that, when ingested, inhaled, or touched, causes an allergic reaction and, (c) airborne volatile organic compounds (VOC) comprising any product that is designed to be sprayed at high pressure in the form of tiny particles that remain suspended in the air. The last category includes many cleaning chemicals, hair spray, various types of primer, and fuels such as gasoline and kerosene, as well as other household, beauty, or hobby products. Some fabrics, particularly those recently manufactured, also contribute to indoor airborne VOCs when they outgas, or leak out chemicals in gaseous form, over time.

Airborne pollutants can build up significantly in indoor environments with the result that the air that we breathe may become contaminated. Considering that on average humans spend approximately 90% of their time in an indoor environment, it will be appreciated that the removal of pollutants from indoor air is of importance to reduce allergies and prevent infection transmission, such as sick building syndrome.

Existing state of the art technologies for the control of airborne pathogens can be categorized as: (a) airborne trapping systems or filters, (b) airborne inactivation systems and, (c) some combination of the above.

Existing airborne inactivation technologies also include those that make use of chemicals, UV radiation and plasma discharge by-products.

Examples of chemical inactivation include the use of antimicrobial vaporizers, typically ozone or hydrogen peroxide. While these systems are effective, they are also disruptive, requiring the evacuation of indoor space to be treated and therefore are not suitable for use under normal living circumstances.

Alternative inventions for the purification of air comprise the use of ultra violet light (UV) emission to kill airborne bacteria. For example, international publication No. WO 2003/092751, describes a device in which a fluid (e.g. air) is passed through an array of UV lamps. It is appreciated that in this solution the one and only inactivation mechanism is via UV radiation.

It is also known to use of plasma radicals for sterilisation of air filter medium; see for example US patent publication No. 2004/0184972 A1. In this prior art document, it is proposed that an upstream plasma discharge can generate active radicals which flow upstream to a medium filter and kill any bacteria or virus trapped by the filter.

In such systems which rely on plasma discharge, the design and configuration of the plasma generator are of particular importance. The teachings disclosed in the present document offers an electrode assembly for plasma generation which can be used for air disinfection and pollution control.

SUMMARY OF THE INVENTION

Accordingly, a first embodiment of the application provides a flexible electrode assembly for an air treatment device as detailed in claim 1.

Accordingly, in one aspect, the present invention provides a flexible electrode assembly for an air treatment device comprising:

a flexible dielectric layer forming an insulating sheet;

a plurality of conductive tracks on a first side of the insulating sheet;

a uniform electrically conducting material with no gaps or holes forming a conductive layer on a second side of the insulating sheet; and an AC power source having a voltage source frequency equivalent to mains frequency and configured to provide power to the electrode assembly such that ionization generated by the assembly is a dark or Townsend type discharge, the power source being further configured to operably ensure that power per unit area applied to the electrode assembly is less than 100 mW/cm$^2$;

and wherein supply of voltage to the conducting tracks and the conductive layer generates plasma which is discharged from the conducting tracks and further wherein the plurality of conductive tracks form a first layer of the assembly and the conductive layer forms a second layer of the assembly, the supply of voltage to the first layer and the second layer generates a dielectric barrier discharge type plasma which is discharged and sustained only from the first layer.

An advantage of the flexible electrode of the present invention is that it can take the form of any desired shape and can conform to the shape of an apparatus into which it is inserted such as the inside of a duct or a ducting section including an apparatus having a generally conical geometry comprising a cylindrical section and a conical section.

In another aspect, the present invention also provides an air treatment system and air treatment apparatus as detailed in the independent claim(s). Advantageous embodiments are provided in the dependent claims.

In a further aspect, the present invention also provides an air treatment apparatus for removal of health threatening airborne pollutants, which may include pathogens, from an air flow, the air treatment apparatus comprising an apparatus having a generally cyclonic-shaped geometry comprising a cylindrical section and a conical section; the apparatus defining an area of generally circular fluid motion, rotating in the same direction, the apparatus having an air inlet for entry of air flow into the apparatus, and the air inlet being configured to facilitate establishing the generally circular fluid motion, and means being provided within the apparatus to inactivate the health threatening airborne pollutants and an exit from the apparatus from which purified outward air can exit. Ideally, in a preferred embodiment, the exit from the apparatus is coplanar with the plane of the direction of the swirling air flow in the apparatus having cyclonic geometry; but the outward air flow direction is opposite from the inward swirling air flow direction. Other features are included in the dependent claims.

An advantage of the air treatment apparatus of the invention is that the spiralling airflow ensures that the pathway of any airborne pollutant material through the apparatus is relatively long so that the time spent in the apparatus is also longer than would be the case with a direct inward airflow longitudinally through the apparatus; hence the number of times that an airborne pollutant material will be urged into the inactivation zone is increased relative to a linear inward airflow. A further advantage is that the outward airflow out of the apparatus then removes the inactivated airborne pollutant material so that no build-up of material occurs inside the cyclone geometry apparatus.

In one preferred embodiment, the present invention relates to an air treatment device comprising a plasma generating flexible electrode and electrostatic precipitator assembly for air disinfection and pollution control wherein the plasma generating flexible electrode electrostatic precipitator assembly comprises the flexible electrode assembly configured for generating low power electrical discharge plasma.

In one aspect, the present invention provides air treatment apparatus comprising: an electrostatic precipitator configured to charge airborne particles in the vicinity of the electrostatic precipitator to provide charged airborne particles; and a plasma generator comprising the flexible electrode assembly, positioned in proximity to but at a predetermined distance from the electrostatic precipitator and configured for cooperation with the electrostatic precipitator, the plasma generator configured to create an inactivation zone in the region of the plasma generator; and wherein the air treatment device comprises means for directing the charged airborne particles generated by the electrostatic percipitator into the inactivation zone such that the air treatment device is adapted to generate charged airborne particles and then immediately, to direct the charged airborne particles into the inactivation zone so as to expose the charged airborne particles to plasma in the inactivation zone. The means for directing the charged airborne particles generated by the electrostatic percipitator into the inactivation zone may comprise a voltage applied between the electrostatic precipitator and the plasma generator such that the air treatment device is adapted to generate charged airborne particles and, at the same time, to direct the generated charged particles, by attracting said charged airborne particles towards the plasma generator, into the inactivation zone so as to expose the charged airborne particles to plasma in the inactivation zone.

It is to be understood that throughout this patent specification, the term, "inactivation zone" refers to a zone in which plasma is released and is effective to inactivate airborne pollutant material including pathogens. Such airborne pollutant material (i.e. airborne pollutants), which can be health threatening, may be subdivided into three groups: (a) airborne pathogens comprising any organism that causes disease that spreads throughout the environment via the air; (b) airborne allergens comprising any substance that, when ingested, inhaled, or touched, causes an allergic reaction and, (c) airborne volatile organic compounds (VOC) comprising any product that is designed to be sprayed at high pressure in the form of tiny particles that remain suspended in the air. The plasma generated by the plasma generator in the air treatment apparatus of the present invention is effective to inactivate any of the airborne pollutant materials as defined in subdivisions (a) to (c).

Thus, the air treatment apparatus is configured to attract the charged airborne particles into the inactivation zone; this is not the same as trying to attract all the charged particles onto the surface of the plasma generator as in fact, such would be undesirable as it could interfere with the effective operation of the plasma generator if all the charged particles were on the surface of the plasma generator. The air treatment apparatus of the present invention comprises a plasma generator, preferably a flexible electrode assembly for generating plasma, which is configured to operate at a power density less than 1 W/cm$^2$ to operably generate a plasma discharge.

In the preferred embodiment, the plasma generator comprises a flexible electrode assembly, flexible electrode assembly which is configured to operate at a power density less than 1 W/cm$^2$ to operably generate a plasma discharge circumferentially about a longitudinal axis of the flexible electrode assembly. It is to be understood that although the flexible electrode assembly may be provided on at least a portion of the inside walls of the air treatment apparatus, preferably, circumferentially about at least a portion of the inside walls, but that the flexible electrode assembly can be of any desired dimensions that is sufficient to provide an inactivation zone in the region of the walls of the apparatus. The inactivation zone extends outwardly from the flexible electrode assembly by up to approx. 1 cm. It is not necessary for the airborne pollutant material to collide with the flexible electrode assembly in order for the airborne pollutant material to be inactivated; it is sufficient for the airborne pollutant material to enter into the inactivation zone. Ideally, in the cyclonic arrangement of the air treatment apparatus of the present invention, airborne pollutant material will enter into the inactivation zone multiple times due to the rotating, swirling motion of the inward airflow. This inward airflow is directed into the air treatment device through an inward airflow port which is configured to establish cyclonic airflow. The airflow port comprises a plurality of walls which cooperate to establish cyclonic airflow.

Most preferably, the plasma generator is configured to be operated at a power density in the range from 0.1 to 0.5 W/cm². This is a relatively low power density for plasma generation and is effective for creating an inactivation zone about the plasma generator.

BRIEF DESCRIPTION OF THE DRAWINGS

The present application will now be described with reference to the accompanying drawings in which are shown, by way of example only, a number of aspects and embodiments of the present invention:

FIG. 2 is a view of the electrode assembly of FIG. 1 from a second side;

DETAILED DESCRIPTION OF THE DRAWINGS

The present teachings relate to an air treatment apparatus comprising a flexible electrode assembly which is used with a ducting system to operably generate a plasma for treatment of air passing through the ducting system. The apparatus may further comprise a power source which is coupled to the flexible electrode assembly to provide power which is used in the generation of a plasma. In addition, an impeller may be required to force air through the ducting system. By providing such a combination of elements, it is possible, when power is applied to the electrode assembly, to generate a low power plasma discharge field to effectively sterilise air of micro-organisms or pathogens or oxidise organic airborne contaminants and particles that are passing through the ducting system.

The power source may be a high voltage generator with voltage output in the range 1 kV to 10 kV amplitude. The high voltage generator may be of continuous (DC) or alternating (AC) current type. An exemplary embodiment is driven by an AC power source. In this embodiment the voltage source frequency is the same as mains frequency, i.e. 50 to 60 Hz depending on the geographical region. In an alternative embodiment the frequency of the power supply may be in the kilo-Hertz range; e.g. 1 kHz to 250 kHz. Further alternative embodiments may be fitted with AC power supplies with modulation frequency in the range above or below those listed above.

Figure 1:
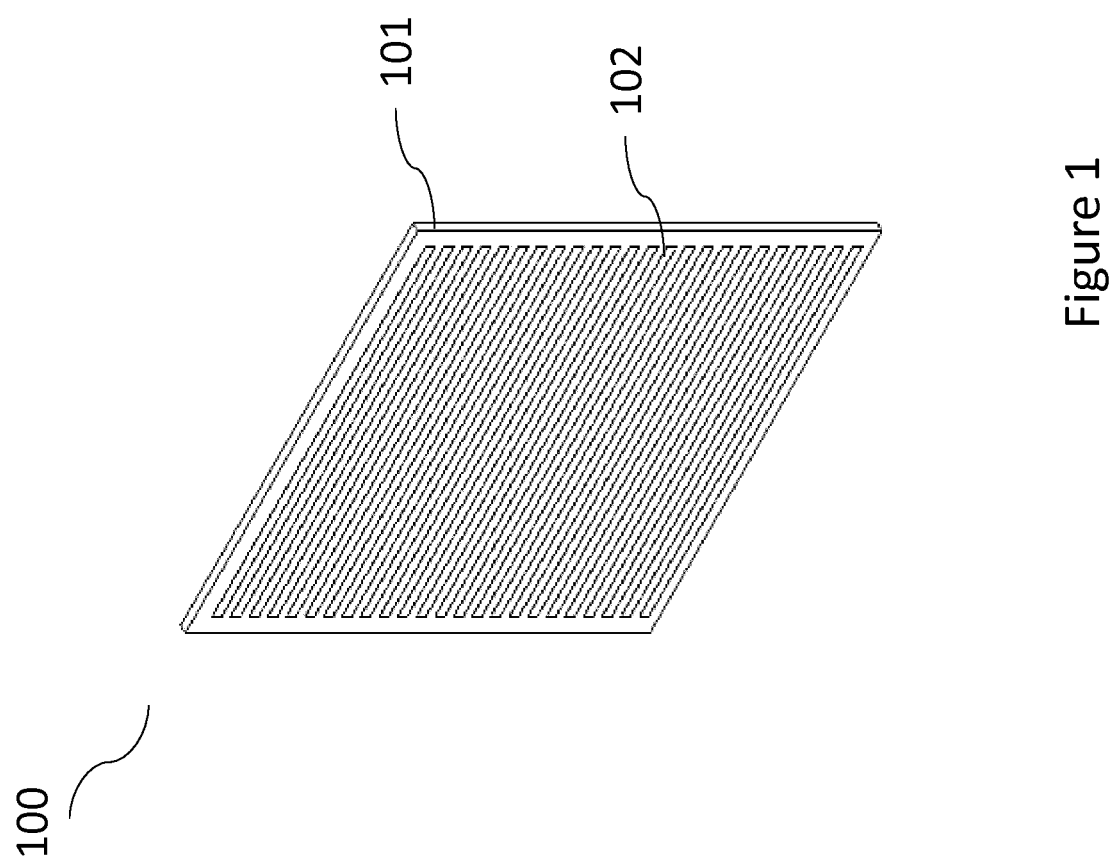
FIG. 1 is a view from a first side of an electrode assembly in accordance with the present teachings.

The configuration of the flexible electrode assembly is best described with reference to FIGS. 1 and 2, which show an electrode assembly 100 comprising a dielectric layer 101 to which electrodes are attached on front and back sides of the dielectric layer 101. In this way, the electrodes are provided on opposing sides of the dielectric layer.

The electrodes each comprise a conductive layer. A first conductive layer 102 is patterned as a series of thin rows of electrically conducting tracks leaving a narrow gap between the rows. The second conductive layer 203 (shown in FIG. 2) comprises a uniform electrically conducting material with no gaps or holes therein. The first 102 and second 203 conductive layers act as a pair of electrodes.

A plasma discharge is generated by applying power to the pair of electrodes comprising the first conductive layer 102 and the second conductive layer 203. The applied power sustains either a DC or an AC discharge from the first surface 102 of the flexible electrode assembly 100. The plasma generation in the present teachings is of a dielectric barrier discharge (DBD) type with both electrodes insulated from one another by the dielectric layer 101. The configuration and positioning of the first 102 and second 203 conductive layers ensures that the plasma discharge is generated and sustained on the first layer 102 of the electrode assembly 100.

Dielectric-barrier discharge (DBD) is an electrical discharge between two electrodes i.e., the first layer 102 and the second layer 203 separated by an insulating dielectric barrier i.e., the dielectric sheet 101. Known DBD devices are typically planar, using rigid parallel plates separated by a dielectric or cylindrical, using coaxial plates with a dielectric tube between them. However, by using flexible materials for the construction of the electrode assembly 100 in accordance with the present teachings, one can assemble an electrode pair with flexible characteristics, thereby allowing the device to be shaped to geometries other than planar or cylindrical arrangements.

The dielectric layer 101 is made of a suitable insulating material with a high dielectric strength, which can be chosen as appropriate by those skilled in the art. In an exemplary arrangement of the present teachings, the dielectric insulating layer 101 comprises a polyimide insulating sheet with dielectric strength greater than 100 kV/mm.

In this exemplary arrangement, the electrode assembly 100 consists of a polyimide sheet with a copper sheet on one side (acting as the second conductive layer 203) and copper tracks on the opposite side (acting as the first conductive layer 102).

The use of polyimide with copper attached thereto is well known for manufacturing printed circuit boards. In particular such configuration may generally constitute a flexible printed circuit board. It is appreciated that such flexible circuits are assembled/manufactured in a planar form and become a bendable or flexible sheet/board arising out of the physical characteristics of the materials used. It is also noted that these bendable boards are typically designed to allow flexibility where traditional rigid printed circuit boards are not suitable; e.g. when conforming to non-planar enclosures or surfaces is required. As such these flexible printed circuit boards are used in similar applications as their rigid counterparts including low voltage and low current usage but heretofore have not been used in the context of a plasma generator.

The inventors of the present application have appreciated that these flexible boards can be configured for use as an electrode assembly or electrode assemblies for generating medium to high power plasma discharges; i.e. discharges where power per unit area is in excess of 1 W/cm$^2$. However, under such operating conditions, the lifetime of such flexible printed circuit boards tends to be reduced due to the high voltage and power applied which may cause short circuiting on the board and burn out the tracks due to high current. Therefore, it is important that the power provided to the flexible printed circuit boards in accordance with the present invention is carefully regulated.

According to the teachings of the present invention, the power applied to the electrode assembly 100 by the power source is to be low enough to limit the amount of ionization of the air in the vicinity of the electrode assembly 100 and to keep low electrical stress on the PCB to ensure long operating lifetimes. In an exemplary aspect, the power per unit area applied to the electrode is below 100 mW/cm$^2$. At this power level, the ionization generated by the system is of the type of a dark or Townsend discharge. As is known to those skilled in the art, this discharge mode is characterized by a combination of low discharge currents (in the range of micro amperes or lower) and no radiative emission, hence the term dark. [see for example Plasma Phys. Control. Fusion 47 (2005) B577-B588]. The generation of radicals in this discharge mode is also limited, which is advantageous in order to maintain a low level of anti-pathogenic agents released by the system of the present invention. The ionized plasma is therefore not of a glow discharge mode where the plasma current and radical and other plasma species concentration is significantly higher resulting in a visible glow, electrode heating and damage and significant release of toxic radicals.

In another aspect, the electrode assembly 100 may include an additional insulating layer between the first conducting layer 102 and the dielectric layer 101. Additionally or alternatively, an insulating layer may be placed between the second conductive layer 202 and the dielectric layer 101. Such an additional layer(s) serves to protect the dielectric layer 101 from external sources of contamination or degradation. The additional protective layer(s) also reduces the possibility of arcing between the layers acting as electrodes and/or nearby conductors.

Figure 3:
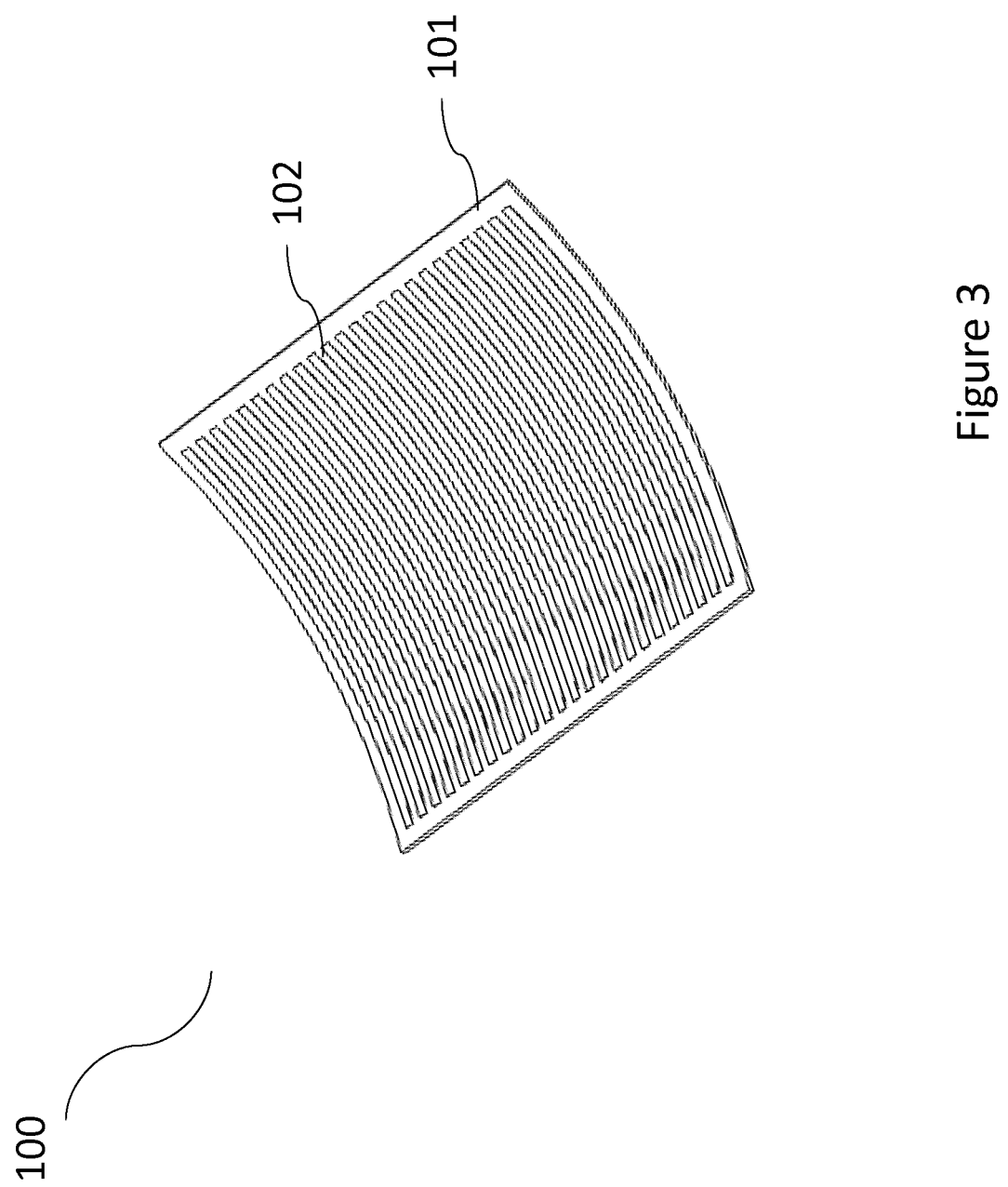
FIG. 3 is a view from the first side of the electrode assembly bent in a semi-circular manner in accordance with the present teachings.
Figure 4:
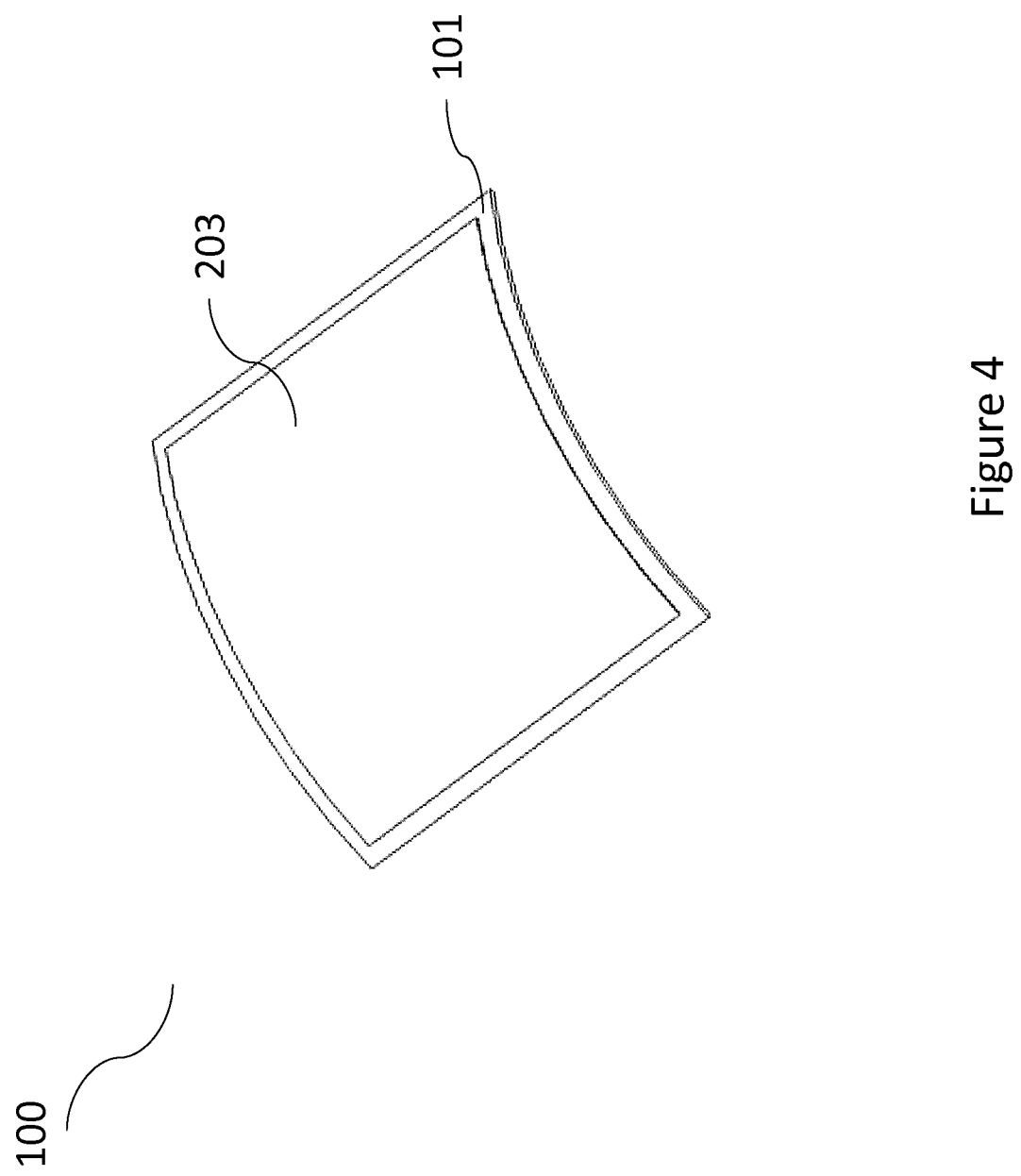
FIG. 4 is a view from the second side of the electrode assembly bent in a semi-circular manner in accordance with the present teachings.

FIGS. 3 and 4 show perspective views of the electrode assembly 100 when bent in a semi-circular manner with the first conductive layer 102 on the inner side and the second conductive layer 203 on the outer side. Specifically, FIG. 3 shows the inner side of the electrode assembly 100 when bent to be arcuate while FIG. 4 shows the outer side of the electrode assembly 100.

Although a semi-circular shape is shown, a plurality of shapes can be formed using the flexible electrode assembly 100. In a preferred embodiment, the shaped formed using the flexible electrode assembly 100 comprises a conical geometry.

It will be understood by those skilled in the art that power is provided from a power supply to the flexible electrode assembly 100. The exact nature of the connection (e.g., wiring) between the flexible electrode assembly 100 and the power supply can be chosen as appropriate and it is not necessary that the power supply and the electrode assembly 100 be co-located. A transformer (not shown) may also be used between the power supply and the flexible electrode assembly 100 to provide high-voltage alternating current.

The first 102 and second 203 conductive layers maintain direct contact around their respective total surface areas with the dielectric layer 101. This ensures that there are no air pockets within the electrode assembly 100 where elevated levels of plasma can build up during generation of plasma.

In the preferred aspect of the present teachings, the continuous uniform material of second conductive layer 203 ensures no plasma is sustained on the second layer 203 of assembly 100. On the other hand, the rows of wire separated by gaps in the first conductive layer 102 allows high electric fields to build up in the gaps due to the high voltage potential applied between the first conductive layer 102 and second 203 conductive layers. This electric field ionizes the gas in the vicinity of the first conductive layer 102 initiating and sustaining an atmospheric plasma discharge. Said plasma discharge is limited to the first surface 102. Furthermore, said plasma discharge generates an inactivation zone above the first conductive layer 102 of the electrode assembly 100 where the plasma field, radiation and active species act as anti-pathogenic agents for the air passing the flexible electrode assembly 100.

An inactivation zone is a zone in which plasma is released and is effective to inactivate airborne pollutant material entrained in the air flow. Health threatening airborne pollutants may be subdivided into three groups: (a) airborne pathogens comprising any organism that causes disease that spreads throughout the environment via the air; (b) airborne allergens comprising any substance that, when ingested, inhaled, or touched, causes an allergic reaction and, (c) airborne volatile organic compounds (VOC) comprising any product that is designed to be sprayed at high pressure in the form of tiny particles that remain suspended in the air.

It will be understood by those skilled in the art that replacing the second conductive layer 203 (i.e., a sheet of conductive material) with a layer similar to that of the first conductive layer 102 (having rows of wire separated by gaps) will result in a plasma discharge being generated and sustained on the second side of the flexible electrode assembly 100 as well as on the front side. This may be desirable under some circumstances and/or applications of the present teachings and it is not intended to limit the present teaching to generation of a plasma on one side only of the electrode assembly.

The flexible electrode assembly 100 should preferably be oriented in a manner that air flows in parallel direction to the direction of the assembly so as to maximise the time that the air is exposed to the plasma that is generated by the assembly. By providing a flexible assembly the inactivation zone that is generated by the electrode assembly does not need to be planar as the assembly may adopt various curved geometries. In particular, due to the flexible nature of the electrode assembly 100 of the present teachings, a plurality of configurations are possible.

Figure 5:
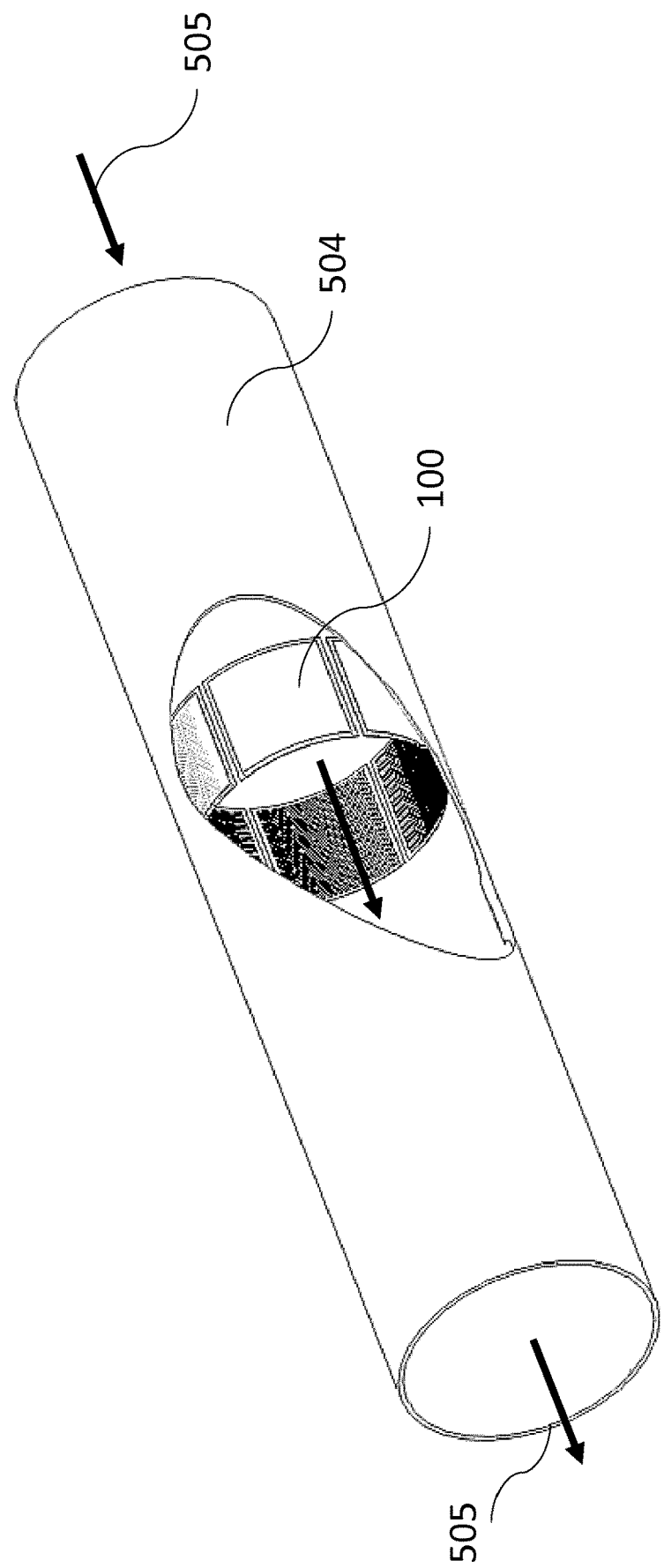
FIG. 5 is a view of the flexible electrode assembly in accordance with the present teachings deployed within a conduit.

FIG. 5 illustrates one such exemplary configuration. It can be seen that a plurality of the flexible electrode assemblies 100 are deployed within a circular conduit 504. The conduit 504 is shown with a cut away for ease of viewing of the plurality of flexible electrode assemblies 100 within the conduit. As will be understood by those skilled in the art any suitable shaped conduit may be used and the flexible nature of the assembly allows it adopt the shape of the conduit 504. Air enters the conduit 504 in the direction of arrow 505, flows past a plurality of electrode assemblies 100 and exits at the other end of the conduit 504.

Figure 6:
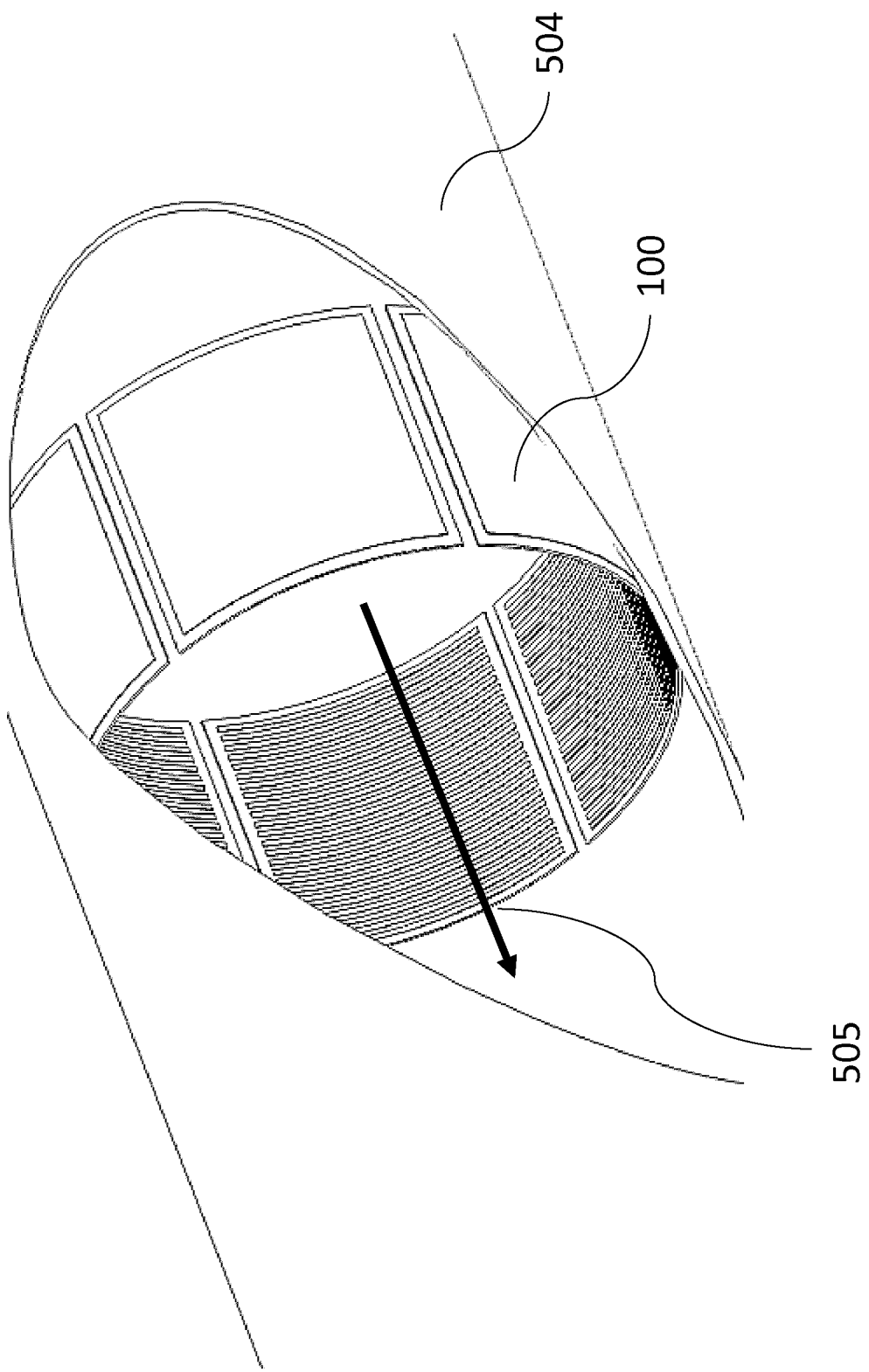
FIG. 6 is a close up view of the flexible electrode assembly of FIG. 5 deployed within the conduit.

FIG. 6 is a close up image of the flexible electrode assembly of FIG. 5. It can be appreciated that a plurality of electrode assemblies 100 are shaped to match or adopt the interior curvature of the conduit 104. Furthermore, the individual electrode assemblies 100 can be positioned relative to one another to form a continuous ring of electrode assemblies within the conduit. It should be understood that in some configurations, fewer electrode assemblies 100 may be used. For example, although four assemblies 100 are shown in FIGS. 5 and 6, two or three assemblies 100 could be used in non-contiguous ring. The determination of the number of assemblies may be chosen as appropriate by the skilled person. In some circumstances, a single assembly may be used provided that the inactivation zone created by the plasma discharged from the first layer of the flexible electrode assembly 100 is sufficient to inactivate airborne pollutant material entrained in the air flow 505.

A number of means known to those skilled in the art could be chosen to induce air flow through the conduit 504, for example, an impeller may be used.

The plasma concentration in the inactivation zone, created by the plasma discharged from the first layer 102 of the flexible electrode assembly 100, is be sufficient to effectively inactivate airborne pollutant material entrained in the air flow. Furthermore, the concentration of plasma should decay sufficiently outside the inactivating zone so that the concentration of any anti-pathogenic agents created by the plasma discharge in the cleaned air expelled from the conduit 504 regions of the apparatus is at a physiologically acceptable level.

Figure 7:
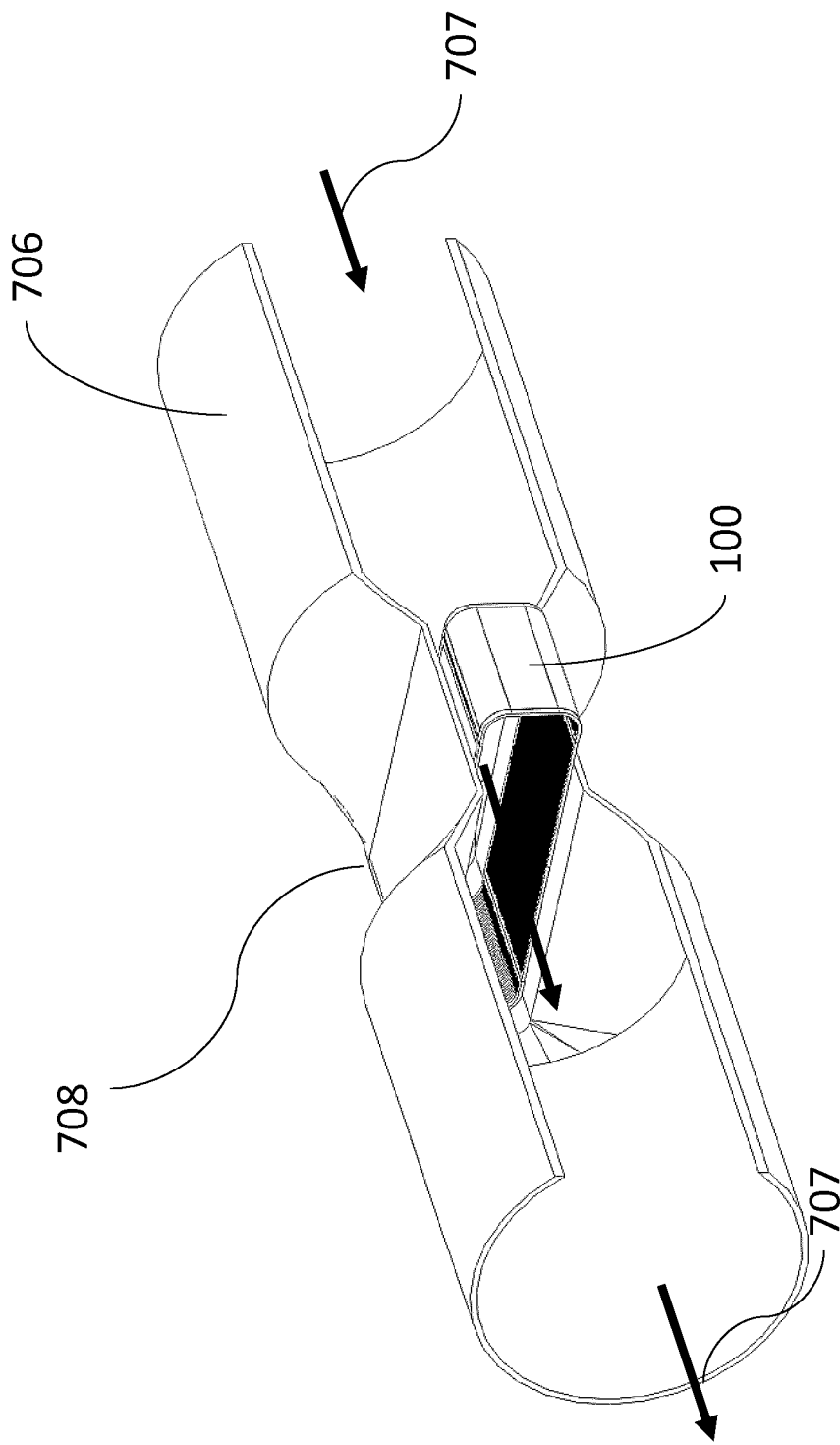
FIG. 7 is a view of an alternative configuration for the deployment of the flexible electrode assembly within a conduit.

FIG. 7 illustrates another configuration for the deployment of at least one flexible electrode assembly 100 within a conduit 706. A cut out section of the conduit 706 is provided in FIG. 7 to for ease of visualization. A plurality of electrode assemblies 100 are provided within a restricted rectangular section 708 of conduit 706. Specifically, the plurality of electrode assemblies 100 are positioned on the interior surface of the rectangular section 708 to form a continuous ring of electrode assemblies. It will be appreciated that the flexible nature of the electrode assemblies ensures that easily configured to form a continuous ring within the rectangular section 708.

Air enters the conduit 706 in the direction of arrow 707, flows into a rectangular section 708 of the conduit 706 fitted with a plurality of flexible electrode assemblies 100. The shape of said section 708 is such that air flowing past the electrode assemblies 100 shall do so within one centimetre from the first conductive layer 102 of the electrode assemblies present in the section 708. This means that the electrode assemblies at the top and bottom interior surfaces of the rectangular section 708 cannot be more than one centimetre apart. However, the distance between the sides can be much more than one centimetre.

Figure 8:
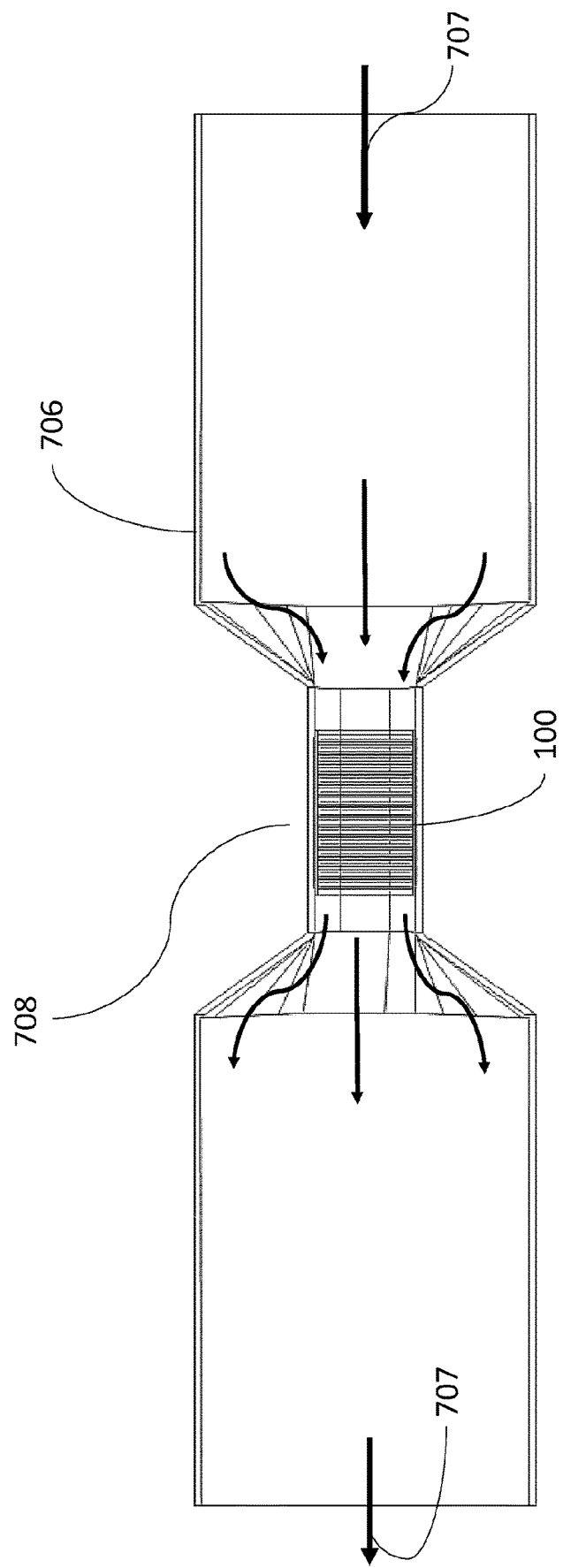
FIG. 8 is a cross section view of the alternative deployment configuration of FIG. 7.

The arrangement of FIG. 7 ensures that any volume of air flowing through the conduit 706 does so within the inactivation zone resulting from the atmospheric plasma discharge. A cross section of the configuration of FIG. 7 is shown in FIG. 8.

Figure 9:
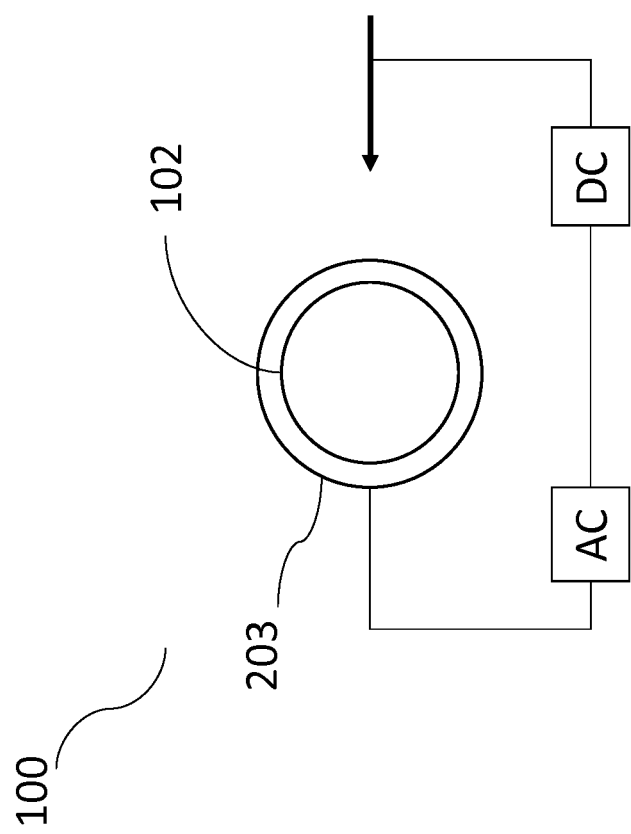
FIG. 9 is a schematic diagram showing the connection for power supply to the first layer of the flexible electrode flexible electrode assembly, that is the plasma-generating surface of the flexible electrode; and the second layer of the flexible electrode assembly, that is the rear side of the flexible electrode.
Figure 20:
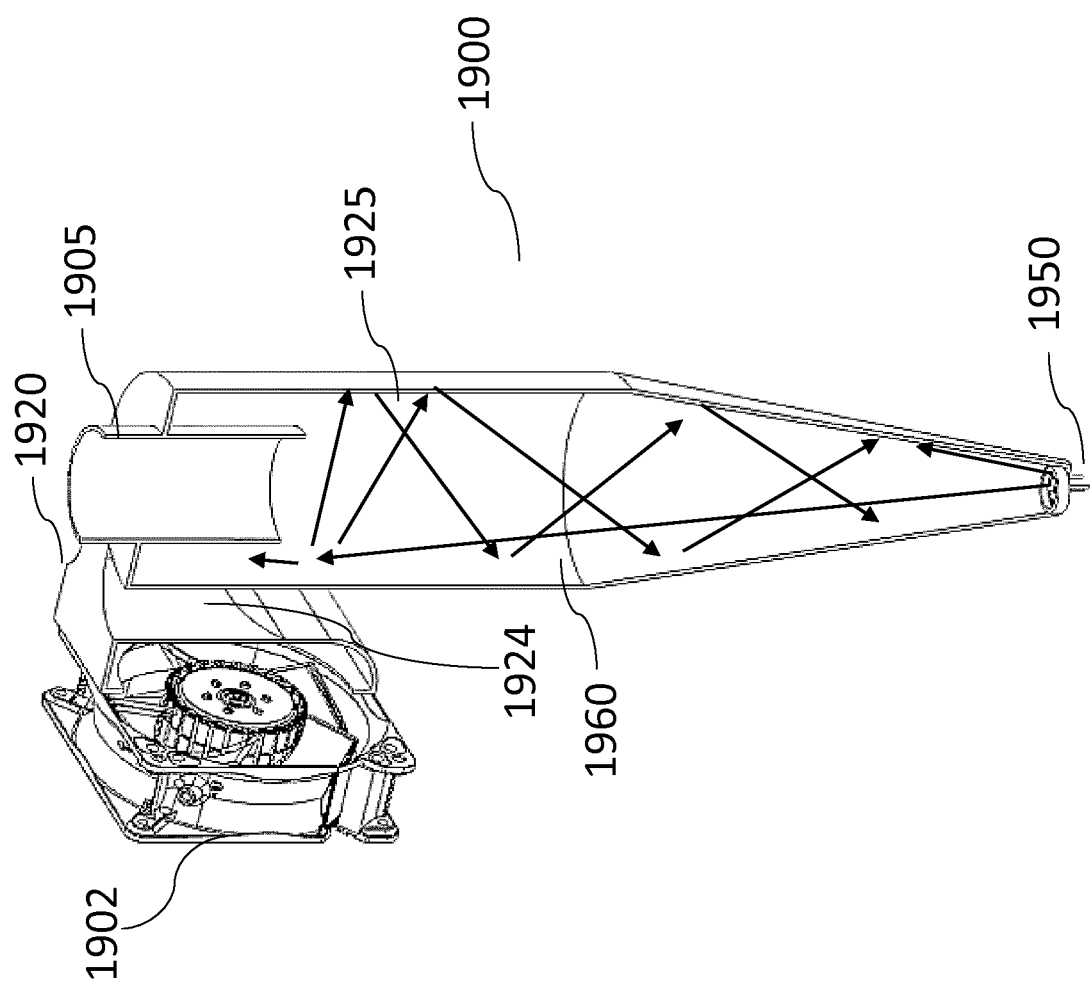
FIG. 20 is an alternative embodiment of the air treatment device shown in FIG. 11 in which a flexible electrode assembly may or may not be included about the walls of the cyclonic geometry air treatment apparatus; in this embodiment, an alternative means of inactivating the health threatening pollutant materials in the air flow is employed, for instance using UV light source and having the inner walls of the air treatment device coated with a UV reflective layer such that the UV light rays from the UV light source reflect internally in the manner shown by the arrows.

We refer now to FIG. 9 which shows the connection for power supply to the first layer of the flexible electrode flexible electrode assembly, i.e. the plasma-generating surface of the flexible electrode assembly; and the second layer of the flexible electrode assembly, i.e. the rear side of the flexible electrode assembly, that is the side of the flexible electrode assembly that is adjacent to the wall of the ducting section or air treatment apparatus. Plasma is generated by the flexible electrode assembly 100 by applying power to the pair of electrodes, that is, the first layer 102 and the second layer 203. The plasma is discharged from only the first layer 102 so as to provide an inactivation zone in the region of the first layer 102. The second layer 203 will typically be abutting against the surface of a portion of an inside wall of a ducting section or air treatment apparatus as will be shown in another aspect of the present invention which will be further described with reference to other Figures herein. The applied power sustains either a DC or an AC discharge between, around and/or on the surface of the electrode pair comprised of the first layer 102 and the second layer 203 of the flexible electrode assembly. It is to be understood that the arrangement shown in FIG. 9 is only one embodiment of the arrangement for the flexible electrode assembly 100 which, by way of example, is shown as being an AC voltage supply to the first layer 102 and the second layer 203. As also shown in FIG. 9, in this particular embodiment, a DC voltage such as in the range of between 1,000 V and 10,000 V (1 kV to 10 kV); preferably in the range of between 2,000 and 9,000 volts; more preferably in the range of between 3,000 and 8,000 volts; most preferably in the range of between 4,000 and 7,000 volts; and ideally, is at a voltage of about 5,000 volts, is applied between the electrostatic precipitator such as the needle electrode array such as in the arrangement shown in FIGS. 20 and 21; and the outer layer 102 of the flexible electrode assembly plasma generator 100.

It will be appreciated that the voltage and current parameters required to achieve a dielectric barrier discharge will depend principally on the nature of the dielectric used. In general, operating voltages below 10 kV are not practical, and preferably, an operating voltage in the range from 1 to 6 kV is provided between the first layer and the second layer of the flexible electrode assembly, most desirably, a voltage of from 3 to 5 kV is provided between the first layer and the second layer of the flexible electrode assembly, for example about 4 kV. It will be appreciated that the current required to maintain the dielectric barrier discharge is significantly less than that required to initiate it. The current (and hence the power) of plasma generator units is normally expressed in terms of the starting current. There should be used a (starting) current in the range from 1 to 10 mA, preferably at least 3 mA. The power of the plasma generator will, of course, depend on the voltage and current combination. The power should generally be not more than 50 watts, and is preferably at least 4 watts. Typically, the power is in the range from 10 to 40 watts. These power levels have in particular been found to be convenient where the plasma generator is used as part of an apparatus unit having a conduit volume of the order of 0.02 to 1.0 m3.

Referring now to FIGS. 10 to 16, a number of embodiments of an air treatment apparatus in accordance with the invention, will be described.

Figure 10:
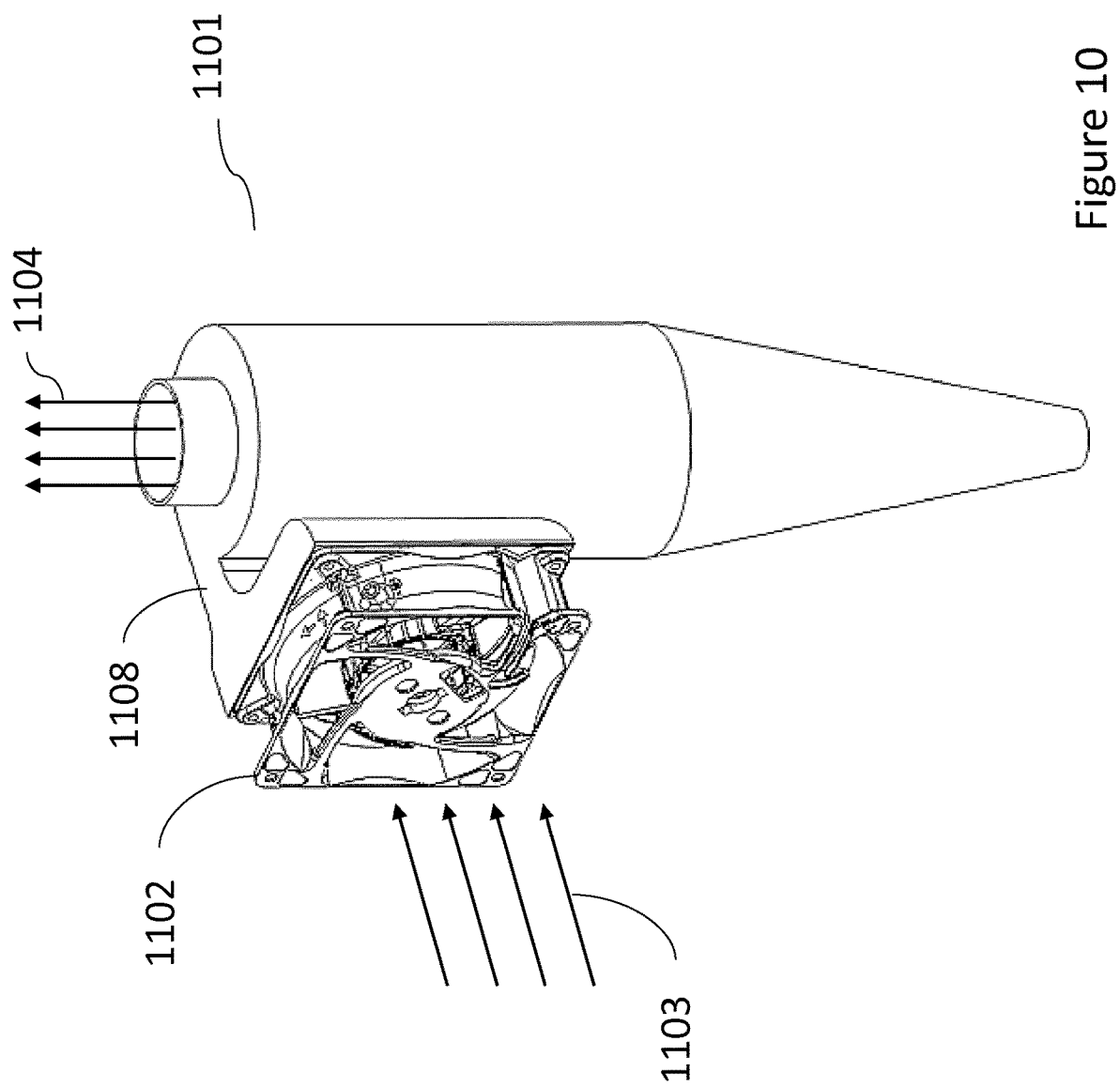
FIG. 10 is a perspective view of one embodiment of an air treatment apparatus which is in a form of a generally cyclonic geometry comprising a generally cylindrical section and a generally conical section.
Figure 11:
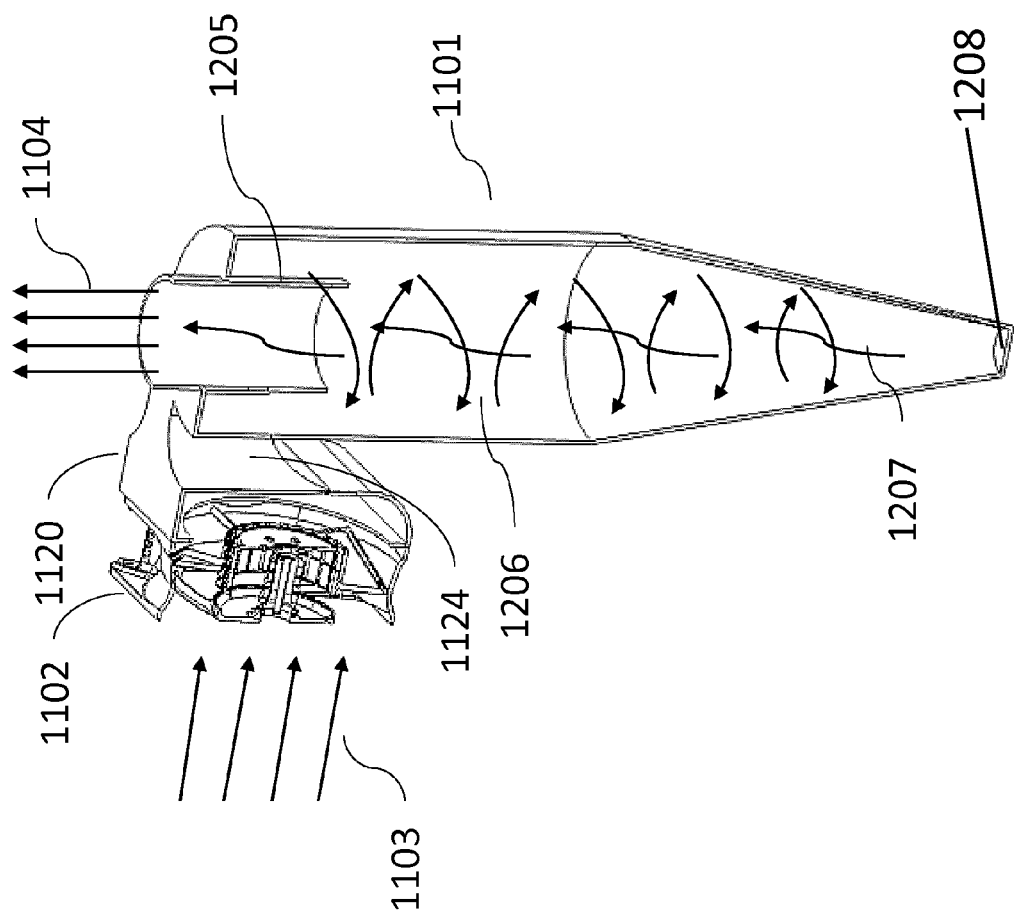
FIG. 11 is a cross sectional view of the air treatment apparatus of FIG. 10 showing the spiralling downwardly inward air flow and the upwardly directed outward air flow.
Figure 12:
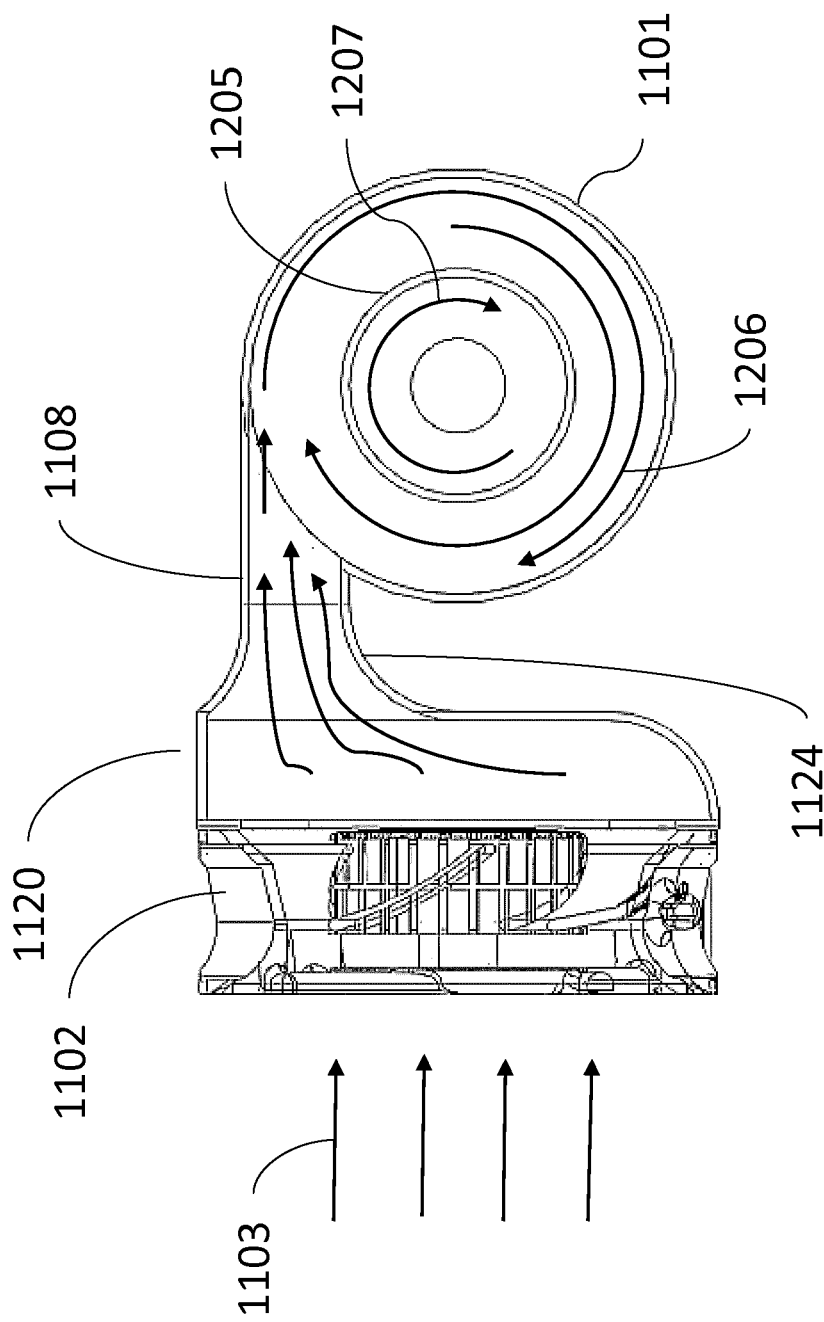
FIG. 12 is a cross sectional view from above, showing the angular airflow inlet arranged tangentially to the direction of the air flow within the cyclonic geometry air treatment apparatus.

The embodiment shown in FIGS. 10, 11 and 12 comprises an impellar 1102 and an air inlet 1108 and the apparatus includes a first section which is generally cylindrical and comprises an airflow inlet; preferably wherein the flexible electrode assembly (not shown in FIGS. 10-12) which is configured adjacent or in abutment with the cylindrical section. The inward air flow as indicated by arrows 1103 enters into the impellar 1102 and through the air inlet port 1120 which has inner walls, including an arcuate wall 1204, configured to established in a spiral, continuously rotating air flow as it travels from the impellar housing 1302 and into the apparatus inlet 1320 which is configured to establish a spiralling airflow which is indicated by the arrows 1206 in the cylindrical section of the apparatus and in the conical section also. Then as the pressure in the closed end 1208 of the conical section increases, the air flow direction is urged back out of the conical section in the direction of the arrow 1207 along the longitudinal axis of the apparatus and out through the exit 1205 as indicated by the arrows 1104. Thus the arrangement has particular advantage as the spiralling pattern of the inward air flow as indicated by the arrows 1106 ensures that airborne pollutant material including pathogens in the airflow will be urged towards the walls of the cylindrical section and the conical section at least once, and more likely, several times during the travel in the spiralling airflow 1206 due to the action of centrifugal forces. Therefore, the airborne pollutant material will be urged into the inactivation zone in the region of the plasma generating flexible electrode assembly provided about the walls of the cyclone geometry.

Figure 13:
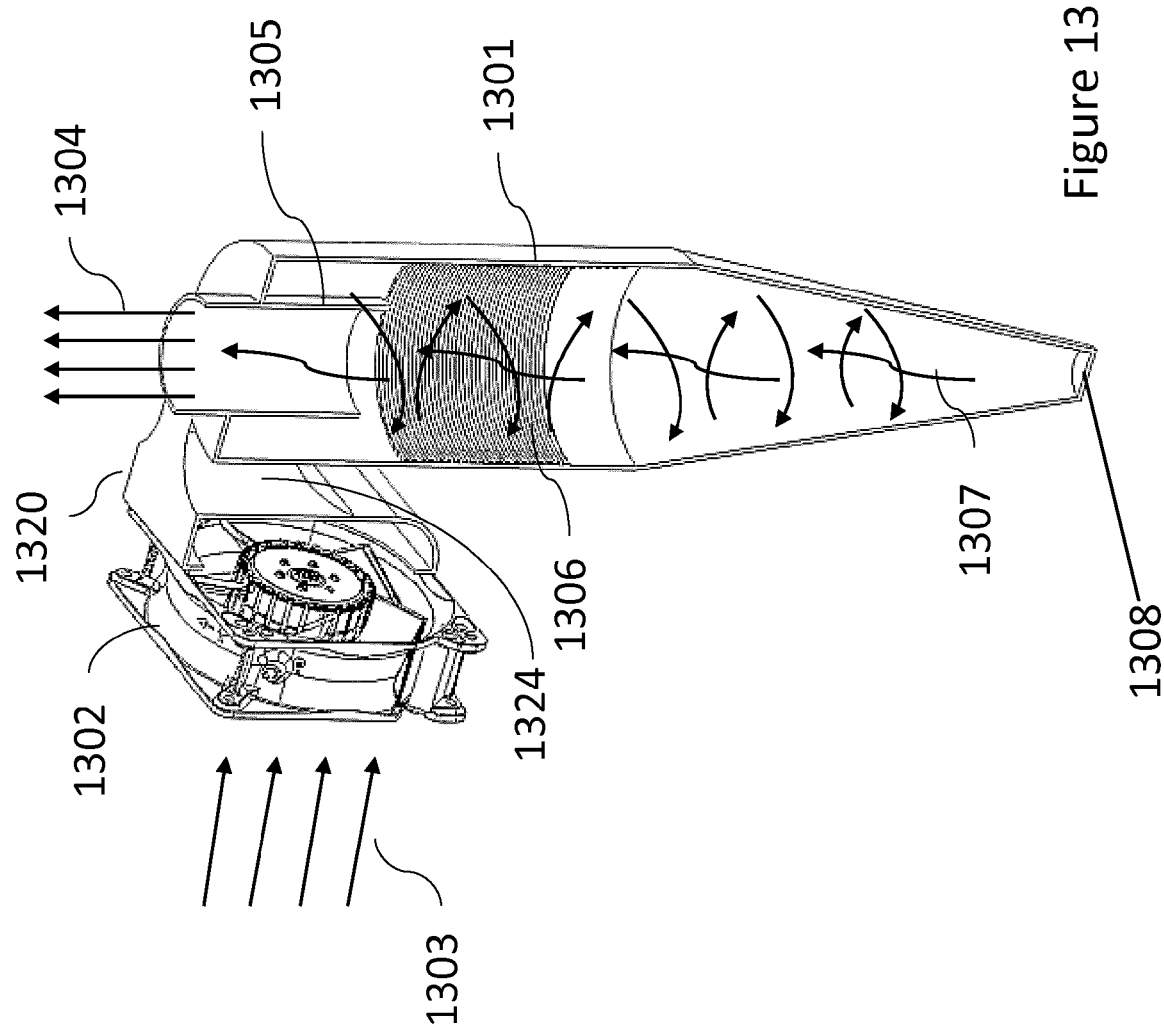
FIG. 13 is a cross sectional view of another embodiment of the air treatment apparatus showing the flexible electrode assembly of FIGS. 1 to 4 shown arranged about the inside walls of the cylindrical section of the cyclonic geometry.

Referring to FIG. 13, the inward air flow 1303 is established in a spiral, continuously rotating air flow as it travels from the impellar housing 1302 and into the apparatus inlet 1320 which is configured to establish the spiralling airflow 1306 in the cylindrical section of the apparatus and in the conical section also. Then as the pressure in the closed end 1308 of the conical section increases, the air flow direction is urged back out of the conical section in the direction of the arrow 1307 along the longitudinal axis of the apparatus and out through the exit 1305 as indicated by the arrows 1304. Thus the arrangement has particular advantage as the spiralling pattern of the inward air flow as indicated by the arrows 1306 ensures that airborne pollutant material including pathogens in the airflow will be urged towards the walls of the cylindrical section and the conical section at least once, and more likely, several times during the travel in the spiralling airflow due to the action of centrifugal forces. Therefore, the airborne pollutant material will be urged into the inactivation zone in the region of the plasma generating flexible electrode assembly 1301 provided about the walls of the cyclone geometry.

Thus the arrangement has particular advantage as spiralling pattern of the inward air flow as indicated by the arrows 1306 ensures that airborne pollutant material including pathogens in the airflow will be urged towards the walls of the cylindrical section and the conical section at least once, and more likely, several times during the travel in the spiralling airflow due to the action of centrifugal forces. Therefore, the airborne pollutant material will be urged into the inactivation zone in the region of the plasma generating flexible electrode assembly 1301 provided about the walls of the cyclone geometry. A further advantage of the air treatment apparatus is that the spiralling airflow ensures that the pathway of any airborne pollutant material through the apparatus is relatively long so that the time spent in the apparatus is also longer than would be the case with a direct inward airflow longitudinally through the apparatus; hence the number of times that an airborne pollutant material will be urged into the inactivation zone is increased relative to a linear inward airflow. A further advantage is that the outward airflow out of the apparatus then removes the inactivated airborne pollutant material so that no accumulation of material occurs inside the cyclone geometry apparatus.

Figure 14:
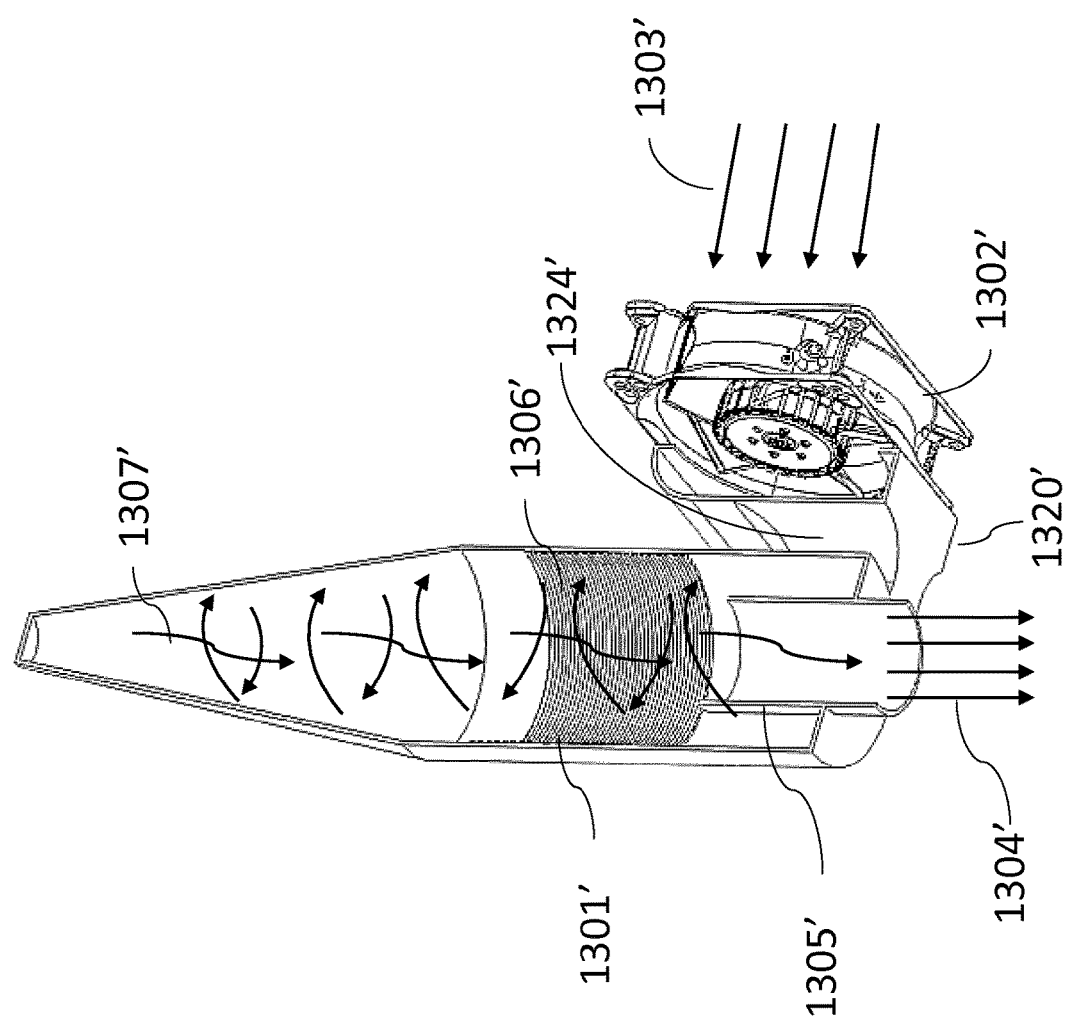
FIG. 14 is a cross sectional view of another embodiment of the air treatment apparatus; which comprises the same features as the embodiment of FIG. 13 except that the apparatus is inverted i.e. turned through an angle of 180 degrees relative to the apparatus as shown in FIG. 13; this demonstrates that the apparatus does not operate in the same manner as a conventional cyclone which is typically used for separation of components and the present invention is entirely different from that function.
Figure 15:
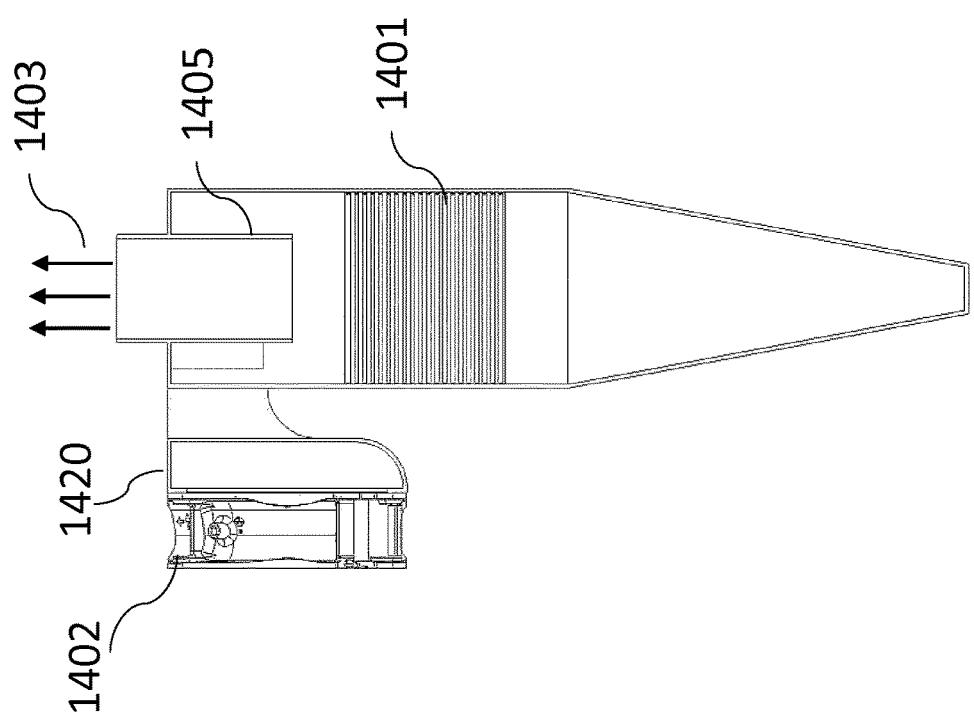
FIG. 15 is a side sectional view of another embodiment, similar to that shown in FIG. 13 with the flexible electrode assembly included.
Figure 16:
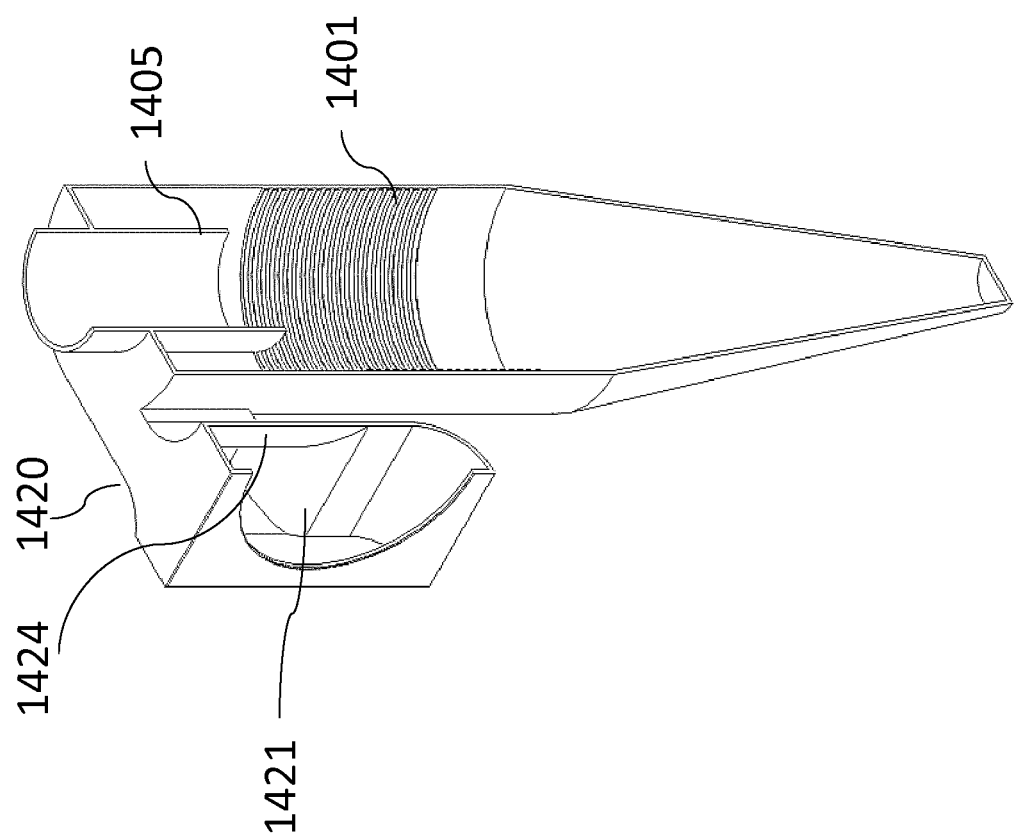
FIG. 16 is a further view of the embodiment shown in FIG. 14.
Figure 17:
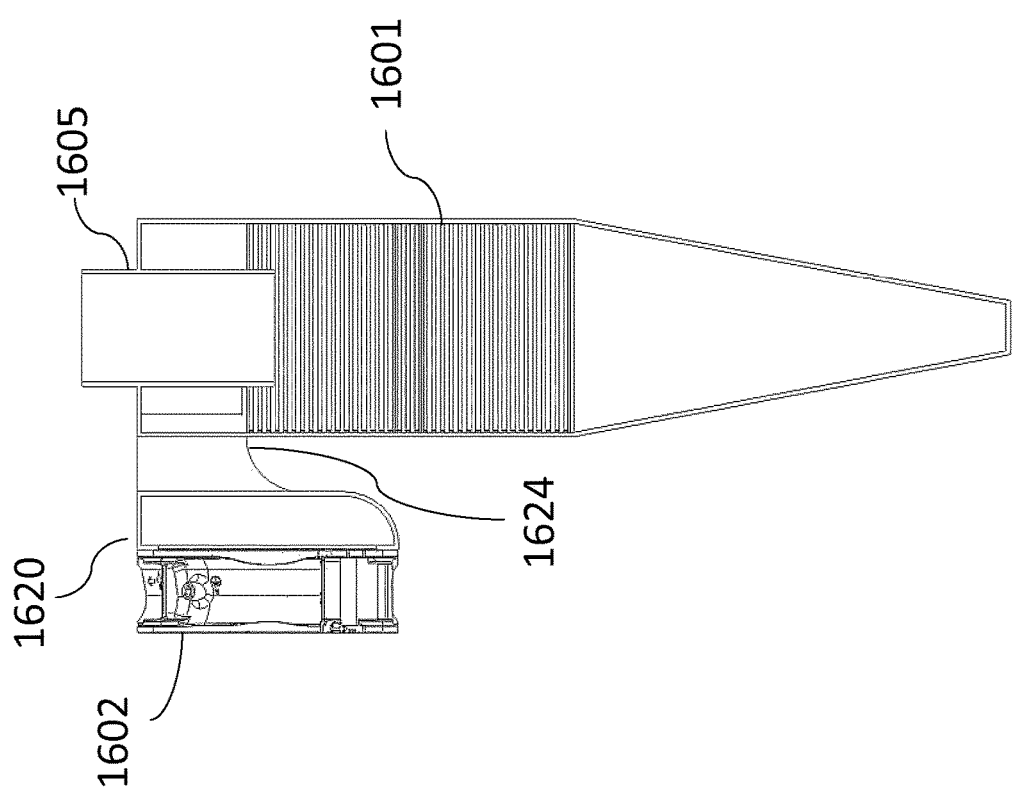
FIG. 17 is a side sectional view of another embodiment, similar to that shown in FIGS. 13 and 15, with the flexible electrode assembly included in the cylindrical section of the air treatment assembly and the flexible electrode extending longer distance along the length of the cylindrical section of the air treatment apparatus.
Figure 18:
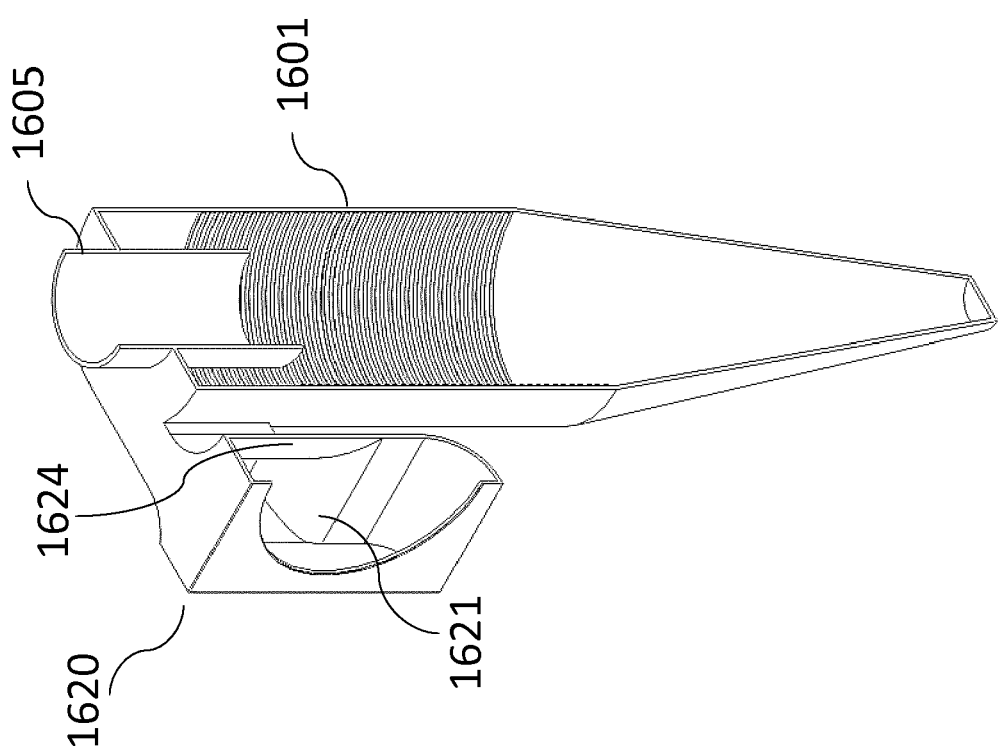
FIG. 18 is a further view of the embodiment shown in FIG. 17.
Figure 19:
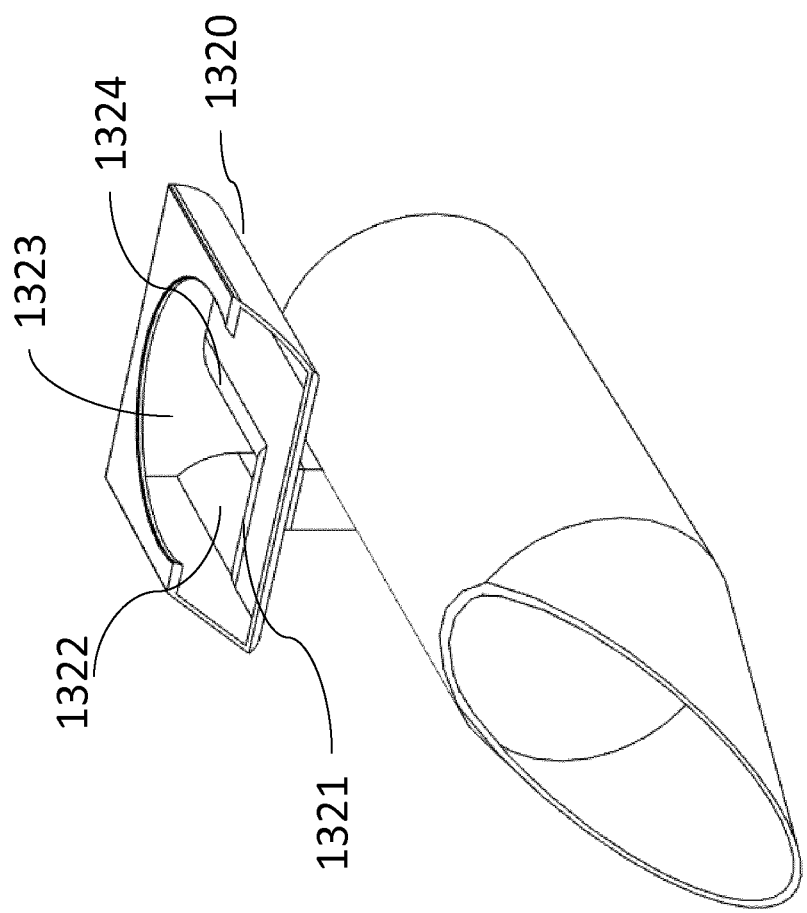
FIG. 19 is an alternative perspective view of the air treatment apparatus of FIG. 13.

Referring now to the alternative embodiment shown in FIG. 14; which comprises the same features as the embodiment of FIG. 13 except that the apparatus is inverted i.e. turned through an angle of 180 degrees relative to the apparatus as shown in FIG. 13; this demonstrates that the apparatus does not operate in the same manner as a conventional cyclone which is typically used for separation of components and the present invention is entirely different from that function. The air treatment apparatus shown in FIG. 14 operates in the same way as described for the embodiment of the air treatment apparatus of FIG. 13. Like features are indicated with like reference numerals to those used in FIG. 13. The cylindrical section includes the flexible electrode assembly having the plasma discharging first layer 1301. Again in this embodiment, the inward air flow 1303' is established in a spiral, continuously rotating air flow as it travels from the impellar housing 1302' and into the apparatus inlet 1320' which is configured to establish the spiralling airflow 1306' in the cylindrical section of the apparatus and in the conical section also. Then as the pressure in the closed end of the conical section increases, the air flow direction is urged back out of the conical section in the direction of the arrow 1307' along the longitudinal axis of the apparatus and out through the exit 1305' as indicated by the arrows 1304'. Thus the arrangement has particular advantage as the spiralling pattern of the inward air flow as indicated by the arrows 1306' ensures that airborne pollutant material including pathogens in the airflow will be urged towards the walls of the cylindrical section and the conical section at least once, and more likely, several times during the travel in the spiralling airflow due to the action of centrifugal forces. Therefore, the airborne pollutant material will be urged into the inactivation zone in the region of the plasma generating flexible electrode assembly 1301' provided about the walls of the cyclone geometry.

Referring now to FIGS. 15 and 16, the air treatment apparatus in this embodiment is substantially the same as that shown in FIG. 13. Like features are referenced with like reference numerals. The air treatment apparatus comprises a cyclone type geometry comprising a cylindrical section and a conical section. The cylindrical section includes the flexible electrode assembly having the plasma discharging first layer 1401. There is an impellar 1402 for directing inward air flow into the inward air flow inlet indicated generally by reference numeral 1420 is established in a spiral, continuously rotating air flow as it travels from the impellar housing 1402 and into the apparatus inlet 1420 which is configured to establish the spiralling airflow (not shown in FIGS. 15 and 16) in the cylindrical section of the apparatus and also in the conical section. As the pressure in the closed end of the conical section increases, the air flow direction is urged out of the conical section along the longitudinal axis of the apparatus and out through the exit 1405. Thus the arrangement has particular advantage as the spiralling pattern of the inward air flow ensures that airborne pollutant material including pathogens in the airflow will be urged towards the walls of the cylindrical section and the conical section at least once, and more likely, several times during the travel in the spiralling airflow due to the action of centrifugal forces. Therefore, the airborne pollutant material will be urged into the inactivation zone in the region of the plasma generating flexible electrode assembly 1401 provided circumferentially about the walls of the cylindrical section of the air treatment apparatus having the cyclone geometry.

It is to be understood that although the flexible electrode assembly is shown in this embodiments in FIGS. 10 to 16 as occupying only a portion of the walls of the cylindrical section of the apparatus, that the flexible electrode assembly can be of any desired dimensions that is sufficient to provide an inactivation zone in the region of the walls of the apparatus. The inactivation zone extends outwardly from the flexible electrode assembly by up to approx. 1 cm. It is not necessary for the airborne pollutant material to collide with the flexible electrode assembly in order for the airborne pollutant material to be inactivated; it is sufficient for the airborne pollutant material to enter into the inactivation zone.

An advantage of the air treatment apparatus of the invention is that the spiralling airflow ensures that the pathway of any airborne pollutant material through the apparatus is relatively long so that the time spent in the apparatus is also longer than would be the case with a direct inward airflow longitudinally through the apparatus; hence the number of times that an airborne pollutant material will be urged into the inactivation zone is increased relative to a linear inward airflow. A further advantage is that the outward airflow out of the apparatus then removes the inactivated airborne pollutant material so that no accumulation/build-up of material occurs inside the cyclone geometry apparatus.

Referring now to FIGS. 17 and 18, an alternative embodiment of the air treatment device from that shown in FIGS. 10 to 16; is exemplified. In the embodiment of FIGS. 17 and 18, the flexible electrode assembly is shown as extending circumferentially about the cylindrical section of the air treatment apparatus and extending axially wider than in the embodiment shown in FIGS. 15 and 16. Thus in this embodiment, the flexible electrode assembly occupies more of the region of the inner wall of the cylindrical section of the air treatment apparatus than in the previous embodiment in FIGS. 15 and 16 . . . . In FIGS. 17 and 18, like features are again referenced with like reference numerals. The air treatment apparatus comprises a cyclone type geometry comprising a cylindrical section and a conical section. The cylindrical section includes the flexible electrode assembly having the plasma discharging first layer 1601. There is an impellar 1602 for directing inward air flow into the inward air flow inlet indicated generally by reference numeral 1620 is established in a spiral, continuously rotating air flow as it travels from the impellar housing 1602 and into the apparatus inlet 1420 which is configured to establish the spiralling airflow (not shown in FIGS. 17 and 18) in the cylindrical section of the apparatus and also in the conical section. As the pressure in the closed end of the conical section increases, the air flow direction is urged out of the conical section along the longitudinal axis of the apparatus and out through the exit 1605.

It is to be understood that the flexible electrode assembly can be extended from the cylindrical section into the tapered section of the cyclonic air treatment device. Indeed, the flexible electrode assembly may, in an alternative embodiment, not shown in the drawings, be provided in the conical section of the apparatus rather than in the cylindrical section.

Indeed, the skilled person will understand that the provision of the flexible electrode about the inner walls of the cyclonic air treatment device can take several forms as the function of the flexible electrode assembly is to generate plasma for effective inactivation of airborne particles that are carried in the airflow into the cyclonic air treatment device; the preferred arrangement is to have the flexible electrode assembly provided about at least a portion of the walls of the apparatus so that the inactivation zone is created about the walls as that is where the centrifugal forces will urge the inward airflow to travel and hence airborne pollutant materials will be urged into the inactivation zone. Hence the provision of the plasma-generating flexible electrode assembly about at least a portion of the walls enables cooperation between the action of the inward airflow pattern and the inactivation zone to ensure multiple entries of airborne pollutant material into the inactivation zone.

Referring to FIG. 19, the air flow inlet carrying air into the cylindrical section is shown in more detail with reference to the embodiment shown in FIG. 13. However, it is to be understood that the air flow inlet shown in FIG. 19 is typical of the construction of the air flow inlet in each of the embodiments shown in FIGS. 10 to 18; and 20 to 22. The air flow inlet is configured to generate a cyclonic type air flow and as such there is an arcuate wall 1323 in cooperation with wall 1324, with the arcuate wall 1323 and 1224 being angled so as to initiate the cyclonic air flow that is a swirling airflow with the inward air flow rotating repeatedly. The airflow inlet also comprises walls 1321 and 1322 which function to direction the inward airflow into the air treatment apparatus.

Referring to FIG. 20, an alternative aspect is shown in which an alternative means for inactivating harmful pathogens and airborne particles is included within the cyclonic air treatment apparatus 1900. In this embodiment, the flexible electrode assembly may be omitted and an alternative means for inactivation such as a UV light source 1950 may be used instead of the flexible electrode assembly. The air treatment apparatus 1900 comprises inner walls coated with a UV reflective layer 1925 so that the UV light from the UV LED 1950 is reflected throughout the air treatment device as indicated by the arrows 1960. The air treatment apparatus 1900 also comprises the impellar 1902 and air inlet port 1924 and air outlet port 1905; thus the airflow direction in the air treatment apparatus 1900 is the same as that shown in FIG. 13 (indicated by the arrows 1306 for the inward spiralling airflow and by the arrows 1307 for the outward linear flow). In this embodiment, the means for inactivating airborne pollutant material comprises the UV light treatment rather than having an inactivation zone created by plasma discharged from the flexible electrode assembly first layer 1301.

However, it is to be understood that, in an alternative embodiment, the UV light source with the inner walls coated with a UV reflective layer to reflect the UV light rays within the cyclonic air treatment device can be used in conjunction with the flexible electrode assembly configured for plasma generation in order to create additional inactivation capability, if desired.

Figure 21:
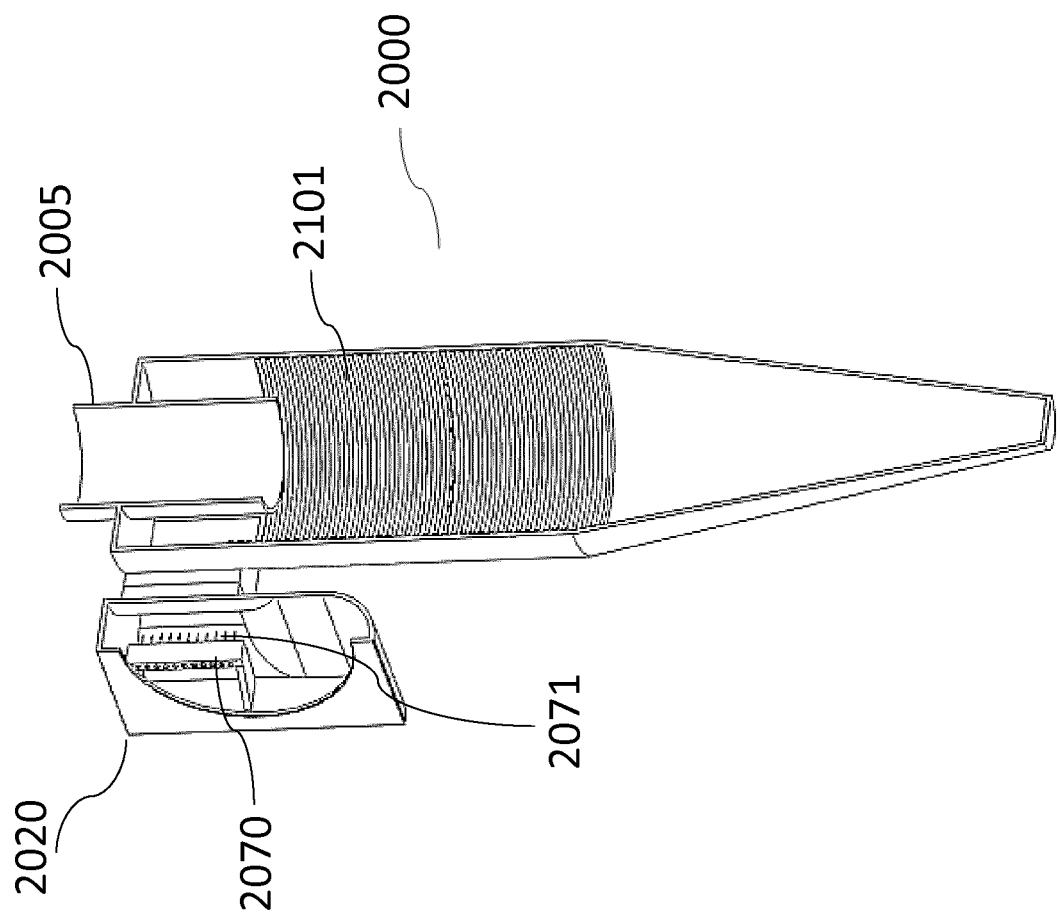
FIG. 21 is a further alternative embodiment of an air treatment apparatus in which an electrostatic precipitator is included in the air treatment apparatus for cooperation with the flexible electrode assembly; the electrostatic precipitator, in this embodiment shown in FIGS. 21 and 22, is in the form of a needle array.
Figure 22:
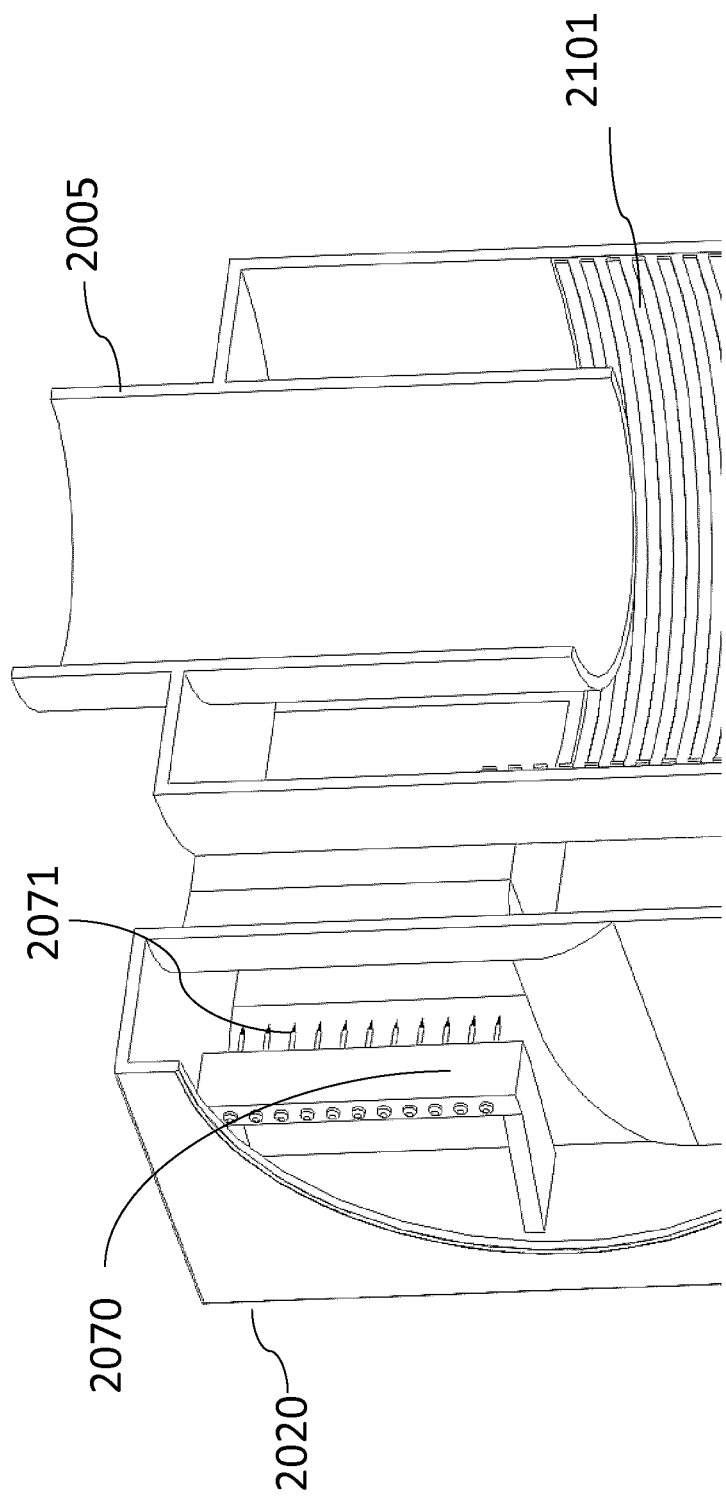
FIG. 22 is an exploded view of the air treatment apparatus of FIG. 21 showing the needle electrode electrostatic precipitator in more detail.

Referring now to FIGS. 21 and 22, a further embodiment of the air treatment apparatus of the present invention will be described. In this embodiment, indicated generally by reference numeral 2000, the air treatment apparatus 2000 comprises a plasma generating flexible electrode assembly having a first layer 2101 for generating plasma and creating an inactivation zone in a region of about up to 1 cm outwardly from the flexible electrode assembly layer 2101. The apparatus 2000 also comprises an electrostatic precipitator 2070 including a needle electrode array 2071 for air disinfection and pollution control in conjunction with the cyclonic arrangement wherein the plasma is generated from the first layer 2101 of by the flexible electrode assembly configured for generating low power electrical discharge plasma. As shown in FIGS. 21 and 22, the needle electrode array 2071 is provided before the inlet port to the cylindrical section of the air treatment apparatus.

In the embodiment shown in FIGS. 21 and 22, the present invention provides air treatment apparatus comprising: an electrostatic precipitator 2070,2071 configured to charge airborne particles in the vicinity of the electrostatic precipitator to provide charged airborne particles; and a plasma generator comprising the flexible electrode assembly with a first layer 2101 for discharging plasma, positioned in proximity to but at a pre-determined distance from the electrostatic precipitator and configured for cooperation with the electrostatic precipitator, the plasma generator configured to create an inactivation zone in the region of the plasma generator; and wherein the air treatment device comprises means for directing the charged airborne particles generated by the electrostatic percipitator into the inactivation zone such that the air treatment device is adapted to generate charged airborne particles and then immediately, to direct the charged airborne particles into the inactivation zone so as to expose the charged airborne particles to plasma in the inactivation zone. The means for directing the charged airborne particles generated by the electrostatic percipitator into the inactivation zone may comprise a voltage applied between the electrostatic precipitator and the plasma generator such that the air treatment device is adapted to generate charged airborne particles and, at the same time, to direct the generated charged particles, by attracting said charged airborne particles towards the plasma generator, into the inactivation zone so as to expose the charged airborne particles to plasma in the inactivation zone.

The inactivation zone is a zone in which plasma is released and is effective to inactivate airborne pollutant material including pathogens. Such airborne pollutant material (i.e. airborne pollutants), which can be health threatening, may be subdivided into three groups: (a) airborne pathogens comprising any organism that causes disease that spreads throughout the environment via the air; (b) airborne allergens comprising any substance that, when ingested, inhaled, or touched, causes an allergic reaction and, (c) airborne volatile organic compounds (VOC) comprising any product that is designed to be sprayed at high pressure in the form of tiny particles that remain suspended in the air. The plasma generated by the plasma generator in the air treatment apparatus of the present invention is effective to inactivate any of the airborne pollutant materials as defined in subdivisions (a) to (c).

Thus, the air treatment apparatus is configured to attract the charged airborne particles into the inactivation zone; this is not the same as trying to attract all the charged particles onto the surface of the plasma generator as in fact, such would be undesirable as it could interfere with the effective operation of the plasma generator if all the charged particles were on the surface of the plasma generator. The air treatment apparatus of the present invention comprises a plasma generator comprising the flexible electrode assembly, which is configured to operate at a power density less than 1 W/cm² to operably generate a plasma discharge.

In the preferred embodiment, the plasma generator is a flexible electrode assembly, most preferably, the flexible electrode assembly, which is configured to operate at a power density less than 1 W/cm² to operably generate a plasma discharge from the flexible electrode assembly.

Most preferably, the plasma generator is configured to be operated at a power density in the range from 0.1 to 0.5 W/cm². This is a relatively low power density for plasma generation and is effective for creating an inactivation zone about the plasma generator.

It is to be understood that combinations of the means for inactivating the health threatening airborne pollutant materials can be included in the air treatment apparatus of the present invention; so that for instance, in an embodiment of the air treatment apparatus, the plasma generating flexible electrode assembly may be provided about at least a portion of the walls of the cyclone geometry and a UV light may be included in the same embodiment of the apparatus and/or an electrostatic precipitator may also be provided in addition. Thus, the embodiments shown are not to be taken as in isolation from each other but may be combined so as to provide effective treatment of airflow.

Furthermore, at least two such air treatment apparatuses may be provides in series so as to provide an array of air treatment apparatuses with the outward airflow from a first air treatment apparatus then being fed into a second air treatment apparatus as the inward airflow for the second air treatment apparatus to ensure efficient air flow treatment.

The words comprises/comprising when used in this specification are to specify the presence of stated features, integers, steps or components but does not preclude the presence or addition of one or more other features, integers, steps, components or groups thereof.

It will, of course, be understood, that various modifications and alterations are possible within the scope of the present invention, as defined in the appended claims.

The invention claimed is:

1. An air treatment apparatus for removal of health threatening airborne pollutants, comprising pathogens, from an air flow, the air treatment apparatus comprising:

a ducting section having a generally cyclonic-shaped geometry comprising a cylindrical section and a conical section, the ducting section defining an area of generally circular fluid motion, rotating in the same direction, wherein the conical section has a closed end;

an air inlet port for entry of air flow into the apparatus, the air inlet being configured to facilitate establishing the generally circular fluid motion;

an exit port in the apparatus;

a plasma-generating flexible electrode disposed about an inner wall surface of the ducting section creating an inactivation zone within the ducting section, wherein the air flow and airborne pollutants are urged into the inactivation zone as the air flow, having generally circular fluid motion, travels in an inward direction through the ducting section in the direction of the closed end of the conical section thereby increasing a pressure of the air flow in the closed end of the conical section and urging the air flow in an opposing outward direction through the ducting section toward the exit port to ensure multiple exposures of airborne pollutant material into the inactivation zone as the air flow travels in the inward direction and in the opposing outward direction whereby purified air exits through the exit port.

2. An air treatment apparatus as claimed in claim 1 wherein the air flow is directed towards walls of the ducting section such that the health threatening airborne pollutants are urged towards and into the inactivation zone created by a plasma discharged from the flexible electrode assembly.

3. The air treatment device of claim 2 wherein the air flow in the inward direction is generally in a spiraling pattern with continuous rotating flow in a plurality of planes as it travels in the inward direction from the inlet through the apparatus to an opposed end of the apparatus;

and the air flow in the opposing outward direction is generally in a single plane along a longitudinal axis of the apparatus, whereby the continuous rotating airflow in a plurality of planes in the apparatus increases exposure of airborne pollutants in the airflow to the plasma-generating flexible electrode inactivation zone ensuring air exposure to the plasma.

4. An air treatment apparatus for removal of health threatening airborne pollutants, which may include pathogens, from an air flow, the air treatment apparatus comprising:

a cylindrical section and a conical section having a closed end and defining an area of generally circular fluid motion, rotating in the same direction, the apparatus having an air inlet for entry of inward air flow into the apparatus, the air inlet being configured to facilitate establishing spiraling air flow motion;

a flexible electrode assembly disposed about an inner wall surface within the conical section creating an inactivation zone to inactivate the health threatening airborne pollutants within the spiraling air flow as the air flow is urged into the inactivation zone; and an air outlet from which purified outward air will exit.

5. An air treatment apparatus as claimed in claim 4 wherein the air outlet from the apparatus is coplanar with a plane of a direction of the spiraling air flow in the apparatus, and wherein an outward air flow direction is opposite from the inward air flow direction.

6. The air treatment apparatus as claimed in claim 4, wherein the flexible electrode assembly comprises:

a flexible dielectric layer forming an insulating sheet;

a plurality of conductive tracks on a first side of the insulating sheet;

a uniform electrically conducting material with no gaps or holes forming a conductive layer on a second side of the insulating sheet; and an AC power source having a voltage source frequency equivalent to mains frequency and configured to provide power to the flexible electrode assembly such that ionization generated by the assembly is a dark or Townsend type discharge, the power source being further configured to operably ensure that power per unit area applied to the flexible electrode assembly is less than 100 mW/cm2;

and wherein supply of voltage to the conductive tracks and the conductive layer generates plasma which is discharged from the conductive tracks and further wherein the plurality of conductive tracks form a first layer of the flexible electrode assembly and the conductive layer forms a second layer of the flexible electrode assembly, the supply of voltage to the first layer and the second layer generates a dielectric barrier discharge type plasma which is discharged and sustained only from the first layer.

* * * * *